United States Patent
Thorne, Jr. et al.

(10) Patent No.: US 12,350,235 B2
(45) Date of Patent: Jul. 8, 2025

(54) CONVENIENCE KITS FOR PREPARING MEDICINE WITH AN ASSURED LEVEL OF SAFETY

(71) Applicant: Thorne Intellectual Property Holdings, LLC, Bountiful, UT (US)

(72) Inventors: Gale Harrison Thorne, Jr., Bountiful, UT (US); Gale Harrison Thorne, Bountiful, UT (US)

(73) Assignee: THORNE INTELLECTUAL PROPERTY HOLDINGS LLC

( * ) Notice: Subject to any disclaimer, the term of this patent is extended or adjusted under 35 U.S.C. 154(b) by 0 days.

(21) Appl. No.: 18/831,055

(22) Filed: May 21, 2024

(65) Prior Publication Data

US 2024/0423873 A1 Dec. 26, 2024

Related U.S. Application Data

(63) Continuation-in-part of application No. 18/445,305, filed on Jun. 26, 2023, now Pat. No. 12,064,394.

(51) Int. Cl.
*A61J 1/20* (2006.01)
*A61J 1/22* (2006.01)

(52) U.S. Cl.
CPC ............ *A61J 1/2086* (2015.05); *A61J 1/201* (2015.05); *A61J 1/2089* (2013.01); *A61J 1/2096* (2013.01); *A61J 1/22* (2013.01)

(58) Field of Classification Search
CPC ........ A61J 1/2086; A61J 1/201; A61J 1/2089; A61J 1/2096; A61J 1/22
See application file for complete search history.

(56) References Cited

U.S. PATENT DOCUMENTS

| | | | | |
|---|---|---|---|---|
| 2,896,381 | A * | 7/1959 | Lange | B08B 9/205 65/109 |
| 4,146,153 | A * | 3/1979 | Bailen | A61J 1/2089 222/91 |
| 4,265,760 | A * | 5/1981 | Abel | A61L 2/022 210/321.87 |
| 4,597,945 | A * | 7/1986 | Sugisawa | A61L 2/06 141/82 |
| 8,449,521 | B2 * | 5/2013 | Thorne, Jr. | A61J 1/16 604/407 |
| 9,149,939 | B2 * | 10/2015 | Zambaux | B25J 21/02 |
| 9,937,288 | B2 * | 4/2018 | Wright | A61M 5/3204 |
| 10,166,686 | B1 * | 1/2019 | Dhanjal | B65B 3/003 |
| 10,390,901 | B2 * | 8/2019 | Godfrey | B65D 25/02 |

(Continued)

*Primary Examiner* — Lucas E. A. Palmer
(74) *Attorney, Agent, or Firm* — Gale H. Thorne

(57) ABSTRACT

A convenience kit being formed by a pair of associated sub-kits which provide capability for bench-top medicine prescription compounding without need for clean room surroundings or such protective equipment as laminar flow hoods. The sub-kits include an exterior sub-kit which provides for access, volumetric measurement and compounding of medicine derived from vials and an enclosing sub-kit housed within a plastic bag which provides a sterile environment for filling a medical treatment vessel for use. The two sub-kits are joined together and communicate by bag entry technology to provide a system which not only protects and, in some cases, provides product sterility, but also assures full containment of all fluid being used in a medical preparation.

7 Claims, 10 Drawing Sheets

(56) References Cited

U.S. PATENT DOCUMENTS

| | | | |
|---|---|---|---|
| 10,555,872 B1* | 2/2020 | Thorne | A61J 1/2096 |
| 10,800,556 B2* | 10/2020 | Thorne | A61J 1/05 |
| 10,940,087 B2 | 3/2021 | Thorne et al. | |
| 11,312,605 B2 | 4/2022 | Thorne, Jr. et al. | |
| 11,744,564 B2* | 9/2023 | Damiano | A61B 17/00234 206/438 |
| 2009/0182263 A1* | 7/2009 | Burbank | A61J 1/2003 210/767 |
| 2009/0194453 A1* | 8/2009 | Thorne, Jr. | A61M 39/16 206/571 |
| 2009/0306621 A1* | 12/2009 | Thome, Jr. | A61M 39/223 604/82 |
| 2014/0305544 A1* | 10/2014 | Chong | A61J 1/20 141/65 |
| 2015/0011963 A1* | 1/2015 | Fangrow | A61J 1/1493 604/414 |
| 2016/0015889 A1* | 1/2016 | Caquias | A61J 1/10 604/87 |
| 2016/0166760 A1* | 6/2016 | Orofino | B65B 5/068 604/416 |
| 2017/0027817 A1* | 2/2017 | Thorne, Jr. | A61J 1/16 |
| 2017/0245956 A1* | 8/2017 | Abu-moustafa | A61B 50/30 |
| 2018/0037343 A1* | 2/2018 | Procyshyn | B65B 3/003 |
| 2018/0221564 A1* | 8/2018 | Patel | B65B 55/10 |
| 2018/0282008 A1* | 10/2018 | Diaz Guerrero | B65B 55/027 |
| 2019/0240112 A1* | 8/2019 | Okonski-Fernandez | A61B 50/37 |
| 2019/0329196 A1* | 10/2019 | Hurst | A61J 1/2003 |
| 2020/0054523 A1* | 2/2020 | McDowell | A61J 1/1462 |
| 2020/0130873 A1* | 4/2020 | Thorne | B65B 3/04 |
| 2020/0146932 A1* | 5/2020 | Schuck | A61J 1/1456 |
| 2020/0337946 A1* | 10/2020 | Thorne | A61J 1/16 |
| 2021/0139834 A1* | 5/2021 | Raviv | C12M 25/16 |
| 2022/0002133 A1* | 1/2022 | Thomas, Jr. | B65D 1/36 |
| 2022/0219842 A1* | 7/2022 | Ward | B65B 3/003 |
| 2022/0378656 A1* | 12/2022 | McLoughlin | B01F 33/846 |

* cited by examiner

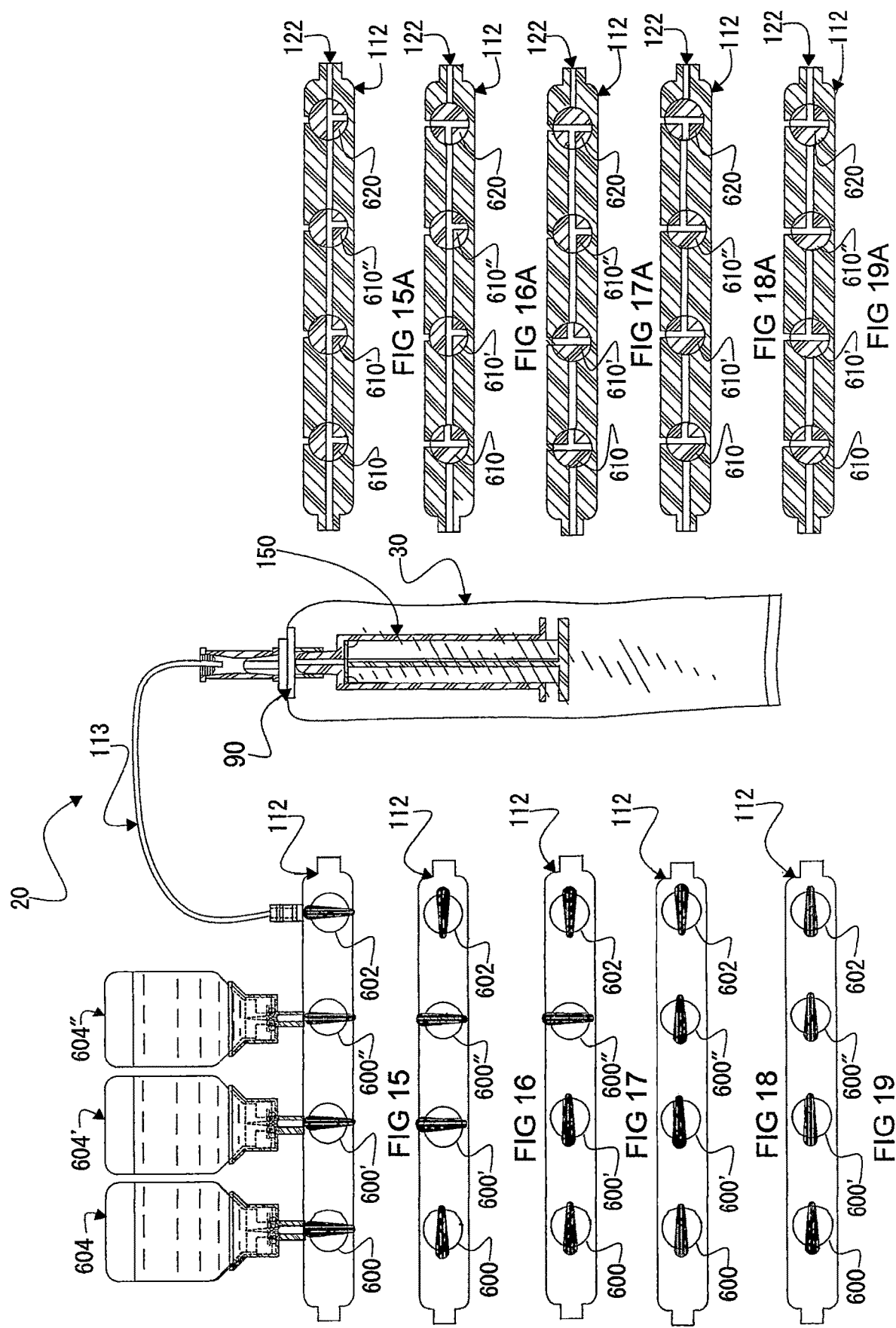

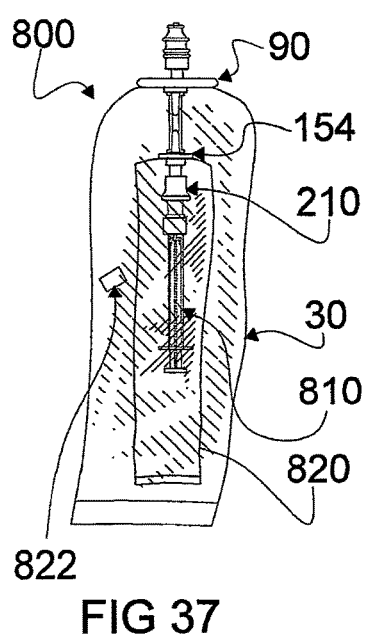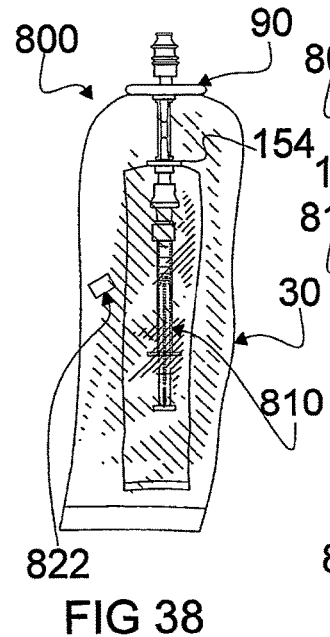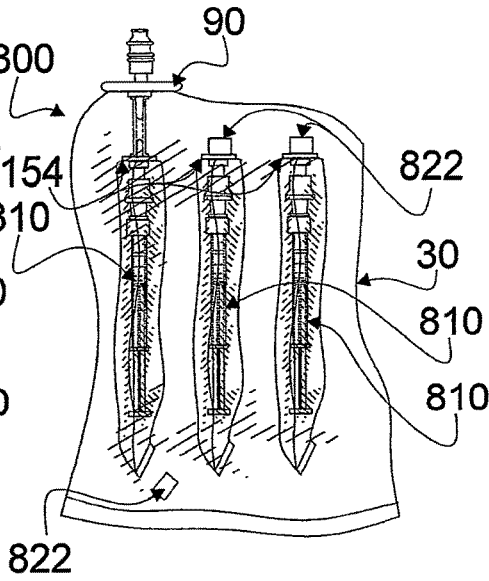
FIG 37      FIG 38      FIG 39
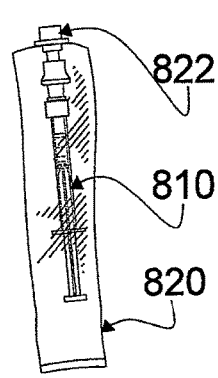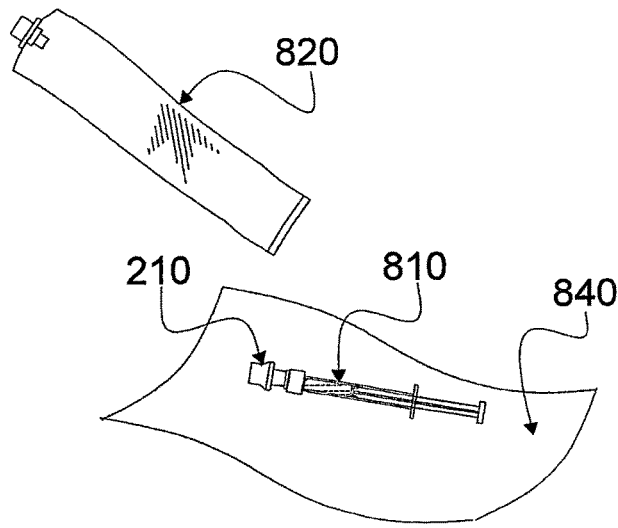
FIG 40
FIG 41

CONVENIENCE KITS FOR PREPARING MEDICINE WITH AN ASSURED LEVEL OF SAFETY

CONTINUITY

This U.S. patent application Continues-In-Part from U.S. patent application Ser. No. 18/445,305 titled CONVENIENCE KIT METHODS FOR STERILIZING RAW HAZARDOUS MEDICINE.

FIELD OF INVENTION

Inventions disclosed herein relate generally to single use convenience kits and associated applications for medical procedures involving methods for compounding, sterilizing, and displacing medicine into dispensing vessels which require controlled conditions in preparation, storage and pre-use. Convenience kits and methods of use disclosed in this patent application are specifically designed for providing protective procedures and entirely enclosed apparatus for user safety when compounding medicine, especially when compounding hazardous medicines. Such kits can be used in a potentially contaminating environment and still produce a desired product with safety. Therefore, the field of invention is particularly related to pre-sterilized kits and to methods which employ preassembled, commercially tested and certified parts used for making convenience kits for compounding medicines. Such convenience kits provide protection and safety both within a protective enclosure of a closed and sealed plastic bag and other apparatus disposed exterior to the bag. Exterior apparatus is designed to have only wholly enclosed fluid pathways throughout. Fluid communication between parts in the interior of the plastic bag and exterior to the plastic bag being via BET or BEST technology. Such convenience kits are single use primarily for compounding a single medical product, thereby being capable of providing an uncontaminated product with a desired SAL, without requiring employment of a laminar flow hood or other sterilization assurance level (SAL) product manipulating devices.

Such kits, made according to instant inventions disclosed herein, are particularly applicable for compounding medicines which can be hazardous, which are often very costly and can have short effective lifetime after being compounded. Each convenience kit is a single-use tool which is specifically designed and assembled to be used in preparation of one particular prescription per kit use. Inventions disclosed herein are also related to methods and apparatus for transferring raw medicine, supplied in bulk in a container such as a medical vial, sterilizing the medicine en-route to displacing the medicine into a vessel for use, while assuring the medicine, being displaced is displaced and, when possible, sterilized, and then disposed in a capped, closed container before being displaced into a potentially contaminating environment. In general, methods and apparatus, disclosed herein, are meant to be used for transferring, or, in some way, altering concentration or character of the medicine following known current validated medicine preparation techniques and not, in any way, for producing a new version of the medicine. As medicine preparation is the field of use of convenience kits made and used according to disclosure in this patent application, it should be noted that devices and procedures detailed herein for creating and/or protecting a desired sterile state should be analyzed by personnel of competent professional organizations relative to requirements specified in both USP 797 and USP 800 and found to be non-inferior to such requirements.

DESCRIPTION OF RELATED ART

Related art providing convenience kits which produce sterilized medicine products via sterilization by filtering media as it is communicated into a pre-sterilized and closed plastic bag (clean room in a bag technology) is known and products for such are available commercially. However, there is no known medical compounding convenience kit product which provides an entirely closed convenience kit product which protects and can provide either, a sterile or a no further contaminated, compounded product and while assuring safety against both uncontrolled release of liquid and gaseous states of all hazardous forms of medicine associated with compounding.

Plastic bags having access only through BEST are disclosed as found in the U.S. patent application from which this U.S. patent application continues in part. However a BET use associated with a closed plastic bag is not known to have been previously used or disclosed. Using BEST, direct entry by a medical syringe also has been disclosed as is, by example, found in U.S. patent application Ser. No. 18/445,305 titled CONVENIENCE KIT METHODS FOR STERILIZING RAW HAZARDOUS MEDICINE. However, there is no known disclosure which teaches enclosing any or all completely enclosing devices exterior to a plastic bag which have BET or BEST interface for communicating fluid into a plastic bag, and, as stated supra, there is no known convenience kit art which provides enclosure of all devices and all fluid pathways while compounding a medicine.

Table of Definitions

Following is a table of a list of words and phrases with definitions clarifying their use in this document:

at least one, n: one or more.

BEST. n: an acronym for a "Bag Entry with Sterilizing Technology" which employs a sterilizing grade (0.2 micron) filter as a processing component in the fluid entry pathway of the plastic bag for sterilizing fluids communicated into the bag, thereby assuring retention of a desired SAL for all things internal to the sealed, presterilized bag and contents.

BET, n: an acronym for a plastic "Bag Entry Technology", i.e. a technology for providing only fluid entry into an associated bag via an assembly of components affixed to the bag which is otherwise closed and sealed after component enclosure to, thereby, deter contamination by digital and other contaminating contact and provide protection from potentially harmful substances which might otherwise find their way into the bag. BET is generally used in for medicine which cannot be effectively sterilized via a medical grade filter.

cap, n: a device used to cover an otherwise exposed orifice of a syringe or other container to maintain sterility of syringe contents thereby.

compounding, v. a process for mixing medicine to fill a prescription for patient use. Generally, the definition includes communicating compounded medicines to a delivery container which is capped to retain medicine and sterility.

dripless connector, n: a device with a fitting disposed as a communicating fluid link with a receiving passageway or container, as an example a syringe, for filling and, thereafter, when being detached, does so without spillage or communication of fluid into the surrounding environment.

Enclosing sub-kit, n: a principle part of each convenience kit made according to inventions disclosed herein, the enclosing sub-kit being fully enclosed and pre-sterilized within a plastic bag or other enclosing apparatus with at least one vessel disposed therein for receiving medicine and being capped before being accessed from the apparatus for use in a medical procedure. The enclosing sub-kit specifically being part of a convenience kit and being securely adjoined to an exterior sub-kit which is used to access, compound and dispense medicine into the at least one vessel within the enclosing sub-kit while retaining desired SAL and for doing so without uncontrollable release of any form of the medicine into the surrounding environment.

Exterior sub-kit, n: a principle part of each convenience kit made according to inventions disclosed herein, the exterior sub-kit comprising apparatus for accessing medicine from medical vials in measured amounts and mixing, dispensing and, when appropriate, assuring sterilization to a desired SAL of a medical preparation compounded and dispensed into an enclosing sub-kit. The exterior sub-kit, being pre-sterilized, and specifically being part of a convenience kit and being securely adjoined to an enclosing sub-kit which is used to receive and cap medicine dispensed into a closable vessel for use in a medical procedure without uncontrollable release of any form of the medicine into the surrounding environment.

filling, v: displacement of liquid into a vessel (e.g. a syringe) generally limited to an amount consistent with a desired quantity of medicine prescribed to be displaced into the vessel.

filter, n: a sterilizing filter which is designed to sterilize all fluid which is passed there through, such filters generally have a 0.2 micron filtering capability and thereby filtering all fluids until becoming wet when the filter will no longer pass gas. This inherent gas blockage feature is commonly used to test filter efficacy by a "bubble test" performed at the end of a liquid sterilizing medical transmission.

filter assembly, n: a fluid transmission assembly, consisting of a filter and other parts, having a purpose of communicating fluid into a convenience kit bag via a closed pathway such that only raw medicine derived from a source is dispatched as a sterile product to an internal source vessel disposed in a sterile environment inside a kit bag, for example, using bag entry sterilizing technology.

fitting, n: a fluid pathway connecting device for medical fluids, generally a luer connector which is well known in medical art.

Hazardous medicine, n: Medicine for treating a patient disease state; such medicine being considered dangerous upon direct liquid or solid state contact or when inhaled as vapor of a gas state.

kit bag (bag), n: a plastic bag, being a part of a convenience kit, used for providing a protected space wherein a closed (sterile) environment disposed therein provides for safe and effective compounding for a prescribed medicine, the bag being made from pliant, preferably transparent material which is strong enough to resist rupturing when used as part of the convenience kit and yet sufficiently pliant to provide for manipulation of associated convenience kit devices affixed to and disposed within the bag to be used in a medicine preparation process, the bag, generally, comprising a single hole through which a filter assembly comprising a sterilizing filter communicates sterilized fluid into the bag, the hole being closed and sealed about a portion of the filter assembly by a gasket disposed between a fitting affixed to a part of the filter assembly inside the bag and an exposed surface of the filter exterior to the hole and the bag to assure maintenance of a predetermined SAL within the bag provided by sterilization before use. Generally, two bags are used in a convenience kit assembly, a bag used as an enclosure for the enclosing sub-kit and a bag used for protective cover for the TMD Syringe.

manifold, n: a closed fluid flow control device which provides for fluid displacement control by valves which are switched between closed and open states for drawing medicine from one or more vial adapters into a TMD Syringe, each valve being is used to manually select a vial from which medicine is delivered via the manifold to an exteriorly disposed liquid drawing device, such as a syringe for use in compounding.

raw medicine, n: medicine, supplied for compounding, which, according to manufacturer instructions, may have to be sterilized or handled without further contamination before use.

SAL, n: Sterility Assurance Level.

sterilized, n: a state of sterilization to which a prescribe medicine has been tailored to a desired SAL by methods which can include both light and filtering technology.

syringe, n: a medical syringe used for transferring and displacing fluid in a medical application; each syringe having an elongated barrel having an opening at one end where through a plunger and associated plunger rod are impelled to displace fluid, the barrel having a spout at the other end, preferably comprising a male luer fitting and an orifice through which the fluid is displaced. For constrained and special applications particular specifications may be placed upon the syringe, such as zero dead space or being free of silicone oil.

TFP Syringe assembly, n: a Tethered Fluid Dispensing Syringe assembly provided as part of an exterior sub-kit, a syringe which is a part of the assembly being used for providing various testing, flushing and other fluid displacement uses as specified for medicine preparation in conjunction with a manifold and affixed vials, the syringe being affixed using dripless connector parts as part of an exterior convenience kit to communicate to a manifold via a tether which permits independent syringe rotation for permitting selective dispensing of gas or liquid without displacement of other exterior sub-kit parts.

TMD Syringe assembly, n: a Tethered Mixing and Dispensing Syringe assembly provided as an integral part of an exterior kit for providing selective displacement of fluids, as required for compounding medicine derived from vials affixed to a manifold, and for dispensing medicine into a receiving vessel disposed within an enclosed kit, a medical syringe which is a part of the assembly being bagged for controlled maintenance of all fluids being displaced therein and thereby, with safety of fluid flow communication through BET assembly and a micro-tubing tether which for provides for separately dispensing both liquid and gas from the syringe without displacement of other parts of the exterior sub-kit.

vial, n: a pre-qualified and certified medical container, which is employed to provide a predetermined quantity of medicine for use in a medical preparation, the container being safely enclosed within the container, but accessible via penetrating a container seal (usually a pierceable septum).

vial adapter, n: a pre-qualified medical device used for accessing raw medicine enclosed and sealed in a vial made accessible by penetrating a vial seal with an adapter spike which is an inherent part of the adapter, generally those vial adapters which latch and hold a vial in place after piercing the septum are preferred vial adapter valve, n: a penetrable shield affixed to a vial adapter which covers and encloses the associated vial septum spike, thereby acting to stop flow through the vial adapter spike until a vial is displaced about the spike to pierce the vial seal and the shield, the shield then being displaced and compressed by vial displacing action about the base of the vial spike, to open the valve, provide access to the septum and to ultimately compress the shield against the base of the vial adapter to act as a gasket, permitting only fluid flow through the spike.

BRIEF SUMMARY AND OBJECTS OF THE INVENTION

In brief summary novel inventions disclosed herein alleviate all of the known problems related to compounding a medicine away from special equipment, such as a laminar flow hood, while providing an effective tool for compounding medicine, especially hazardous medicine, with safety. Convenience kits, made according to the present inventions, are particularly useful in preparing a wide range of medicine, including hazardous medicine, for use. Also, problems associated resulting from displacing a freshly prepared medicine container having a contaminated outer surface onto a sterile field are alleviated by providing such a container presterilized inside and outside and so maintained until use.

In general, inventions disclosed herein involve providing two kits joined either by a BET or a BEST assembly to perform a single medical preparation function. A first kit (the exterior sub-kit) has external surfaces which communicate directly with a surrounding environment. However, each exterior sub-kits is designed with completely enclosing internal surfaces for containing and protecting all fluid which is disposed internally. The second kit (the enclosing sub-kit) comprises a totally enveloping plastic bag in which pre-sterilized containers are made available for being filled and capped for providing and using the medicine as prescribed. Using a BEST assembly, the enveloping kit can also sterilize, as well as filling and capping medicine to provide a prescription sterilized to a desired SAL. The plastic bag, of the enclosing sub-kit is pre-sealed and sterilized to assure a realized SAL environment for all medicine dispensed into the bag which is further assured by having only a single pathway through a BET or BEST assembly for fluid flow into the pre-sterilized bag interior. The bag and all interior contents of the kits are pre-sterilized to assure retention of a predetermined SAL of all interiorly communicated and disposed matter.

One exemplary application for the inventions is hazardous medicine preparation, providing for preparing a prescription by compounding a plurality of raw medicines provided in secure containment vessels such as medical vials. As such, as part of an exterior sub-kit, vial adapters, fitted with vial adapter valves or other dripless connectors, assure full raw medicine containment even when a flow control valve is improperly actuated and which might otherwise permit release of the raw medicine from containment into the surrounding environment. A manifold is preferably used for controlled coupling outflow from the vials to a syringe, or other fluid dispensing device, which can be used for measuring raw medicine volumes derived from the vials and for sterilizing and communicating those volumes through a sterilizing filter into patient medicine dispensing vessels. In all cases connecting fittings, which may have exterior exposure, are selected for being proved to be dripless when disconnected; thereby assuring a desired level of kit-use safety. In order for syringes used in the exterior sub-kit to selectively dispense either gas or liquid, without unduly affecting placement of other associated devices, such syringes are tethered to be able to be disposed for selectively communicating either gas or liquid via small diameter, flexible tubing without requiring displacement of other associated exterior apparatus.

Each enclosing sub-kit is made up of a completely enclosing container, such as a plastic bag, which is entirely closed except for a bag entry assembly used to communicate fluid into the bag (using BET or BEST). Using BEST, the bag entry assembly is fitted with a sterilizing medical grade filter to provide a medical grade sterile product when so dispatched into the enclosing bag. Preparatory for use when manufactured, the sterile bag is closed and sealed with contents inside. Thereafter, the bag and all contents are sterilized to a predetermined SAL. Dispensing receptacles within the sterile bag can be medical dispensing containers including elastomeric balls, syringes, and IV bags. At the end of each sterilizing, container filling process, operation of a sterilizing filter is tested (via a bubble test) for operational efficacy to assure product sterility.

Another example of convenience kit application made according to the present invention is providing a product containing medicine container, which is sterile both on the inside and outside. This is accomplished by providing a second enclosing, sterility protecting bag inside an outer plastic bag of the enclosing sub-kit. The inner bag has a BET pathway into enclosed contents, which has the same purpose as the plastic bag mentioned in the first example, but has no required filter assembly. Rather, a closed, single sterile, but releasably connected, pathway and direct communicating flow pathway is provided from a filter assembly of the outer bag into the inner bag and to a dripless connection with the inner bag. Generally, a container for-use in a predetermined medical procedure is filled with prescribed sterilized medicine. Along with all contents of the inner bag, the exterior of the container is pre-sterilized and maintained so by being resident in the closed pre-sterilized inner bag. Note that the inner bag, being closed during filling is maintained in a controlled sterility state through filling of the container. After filling, the bag is preferably closed by a cap over a BET fitting exposed when the inner bag is decoupled from the outer bag (while the inner bag remains within the outer bag). The container thus remains in a controlled sterility state due to residency within the sealed inner bag. As such the inner bag and contents can be removed from the outer bag with assurance of maintenance of total container sterility. For this reason, the inner bag can be transported to a site where sterility must be maintained (e.g. a medical surgery field), the bag opened and the container "dropped" onto the field with assurance of maintained sterility.

It is a principle object to provide a convenience kit which can be used to compound a medical preparation within an open and uncontrolled environment without preparation fluid communication with contamination which can exist exterior to the convenience kit and with full assurance of maintenance of a sterile state of product disposed within closed parts of the convenience kit.

It is a primary object to provide a convenience kit which can be used with safety for the user when compounding hazardous medicine.

It is a major object to provide a convenience kit which provides for compounding a medical preparation, but also which sterilizes associated raw medicine as an inherent part of the compounding process.

It is also an object to provide a convenience kit which can be used for compounding medical preparations, which does not sterilize compounded medicine as an inherent part of the compounding process but which is instrumental in effectively retaining a previous sterile state of the medicine through filling and capping.

It is a principle object to provide a convenience kit for compounding medical preparations which fully contains all components of the medical preparation throughout all compounding steps.

It is a further very important object to provide a convenience kit which can selectively provide not only a sterile product but also a container having a sterile exterior whereby the product and container can be displaced upon a sterile field with assured safety.

It is a major object to provide a convenience kit which meets all requirements of each medicine for which the convenience kit is designed and made for use, including sterilization, compounding and reconstitution without affecting, in any way, the quality, chemistry or performance of the medicine, as prescribed.

These and other objects and features of the present invention will be apparent from the detailed description taken with reference to accompanying drawings.

BRIEF DESCRIPTION OF THE DRAWINGS

FIG. 15 is a schematic diagram of a tethered medical syringe covered and sealed within a plastic bag having but single pathway for fluid communication through a BET assembly which communicates with a manifold which is otherwise seen affixed via a BEST assembly to an enclosing bag in FIG. 1, such syringes being seen tethered to the manifold which selectively communicates with three vial adapters each vial adapter being affixed to a liquid containing vial, the arrow between the enclosing bag and manifold indicating direction of controlled flow from the manifold valve nearest the arrow, the manifold being seen to comprise a plurality of handles for rotating associated valves disposed in the manifold, each of the valves being disposed for communicating control of fluid from an associated vial.

FIG. 15A is a cross section of a portion of the manifold, wherein fully enclosed fluid pathways resulting from valve states of handle positions seen in FIG. 14, are seen.

FIG. 16 is a schematic diagram of manifold switching in a second state of operation relative the manifold state seen in FIG. 14.

FIG. 16A is a cross section of a portion of the manifold, whereby fluid pathways resulting from valve states of handle positions seen in FIG. 16, are seen.

FIG. 17 is a schematic diagram of manifold switching in a third state of operation relative the manifold state seen in FIG. 16, manifold valves being disposed for communicating control of strictly enclosed fluid flow within the manifold.

FIG. 17A is a cross section of a portion of the manifold, whereby fluid pathways resulting from valve states of handle positions seen in FIG. 17, are seen.

FIG. 18 is a schematic diagram of manifold switching in a fourth state of operation relative the manifold state seen in FIG. 17, other manifold valves being disposed for communicating strictly controlled flow of fluid from an associated vial.

FIG. 18A is a cross section of a portion of the manifold, whereby fluid pathways resulting from valve states of handle positions seen in FIG. 18, are seen.

FIG. 19 is a schematic diagram of manifold switching in a fifth state of operation relative the manifold state seen in FIG. 18, other manifold valves being disposed for communicating control of fluid from an associated vial.

FIG. 19A is a cross section of a portion of the manifold, whereby fluid pathways resulting from valve states of handle positions seen in FIG. 19, are seen.

FIG. 37 is a schematic diagram of an enclosing sub-kit which in used is affixed to an exterior sub-kit (not shown) for filling and providing a vessel (in this case a medical syringe) which is sterile inside and outside whereby the vessel can be used within a sterile environment with assurance of safety against contamination.

FIG. 38 is a schematic diagram of the vessel seen in FIG. 37 having been filled via serially affixed BEST and a BET assemblies affixed in series within a sterile environment for providing and protecting both exterior and interior bagged contents from contamination before use.

FIG. 39 is a schematic diagram of a plurality of vessels each being similar to the vessel seen in FIGS. 37 and 38 providing indication that more than one filled vessel can be prepared at a time.

FIG. 40 is a schematic diagram of a single bagged vessel, capped before being access from an outer bag through which a BEST assembly communicates, being protected by an inner bag for safety in transport.

FIG. 41 is a schematic diagram of a totally sterile vessel being dropped upon a sterile field using conventional technique to assure safety in prospective use.

DETAILED DESCRIPTION OF THE ILLUSTRATED EMBODIMENTS

Figure 1:
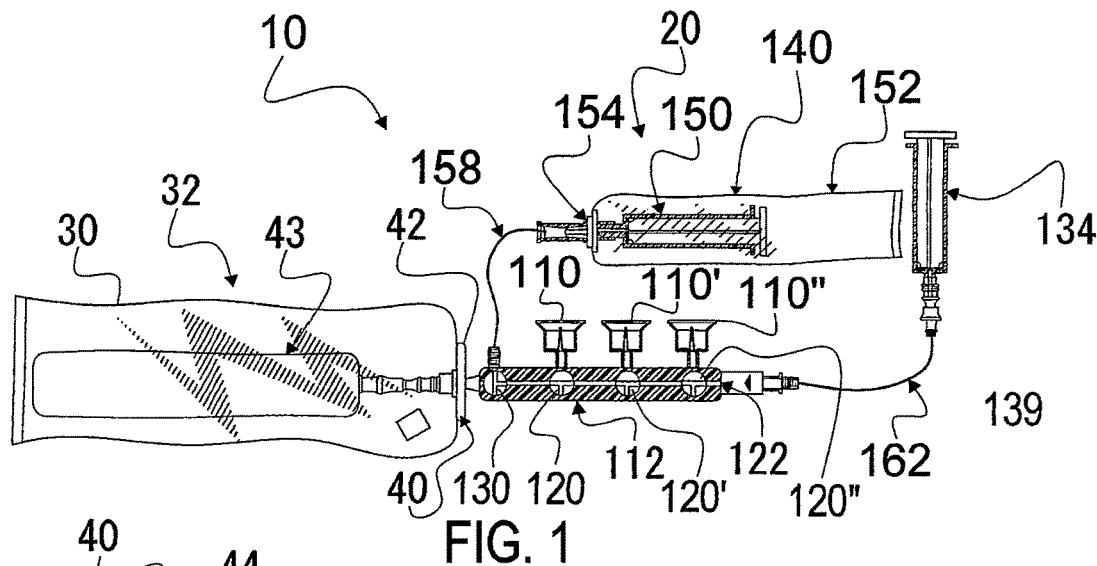
FIG. 1 is a schematic diagram of a side elevation of a convenience kit comprising an enclosing sub-kit securely affixed to an exterior sub-kit made according to instant inventions with a liquid filled IV bag disposed as a single receiving vessel within a sealed bag, a first medical syringe being disposed within a plastic bag (bagged syringe) closed and sealed with via BET to assure containment of all liquids communicated therein and thereby, the bagged syringe being tethered and securely affixed to the enclosing sub-kit via a totally closed pathway and a second syringe tethered to a part of a manifold assembly away from the enclosing sub-kit.

In this description, the term proximal is used to indicate a location of a referenced segment or item associated with a device which is relatively close to an object of a sentence disclosing its position. A term distal, when used, refers a location more distant from the segment or item than that which is proximal. Reference is now made to embodiments illustrated in FIGS. 1-41 wherein like numerals are used to designate like parts throughout. Primes of numbers are indicative of part similarities in application and function, but with noted differences from other like numbered parts. Notably, the following methods for making and using convenience kits, made according to instant inventions disclosed herein, are provided with further objects to provide background and instructive information for understanding manufacture and use of convenience kits which are the subject of this U.S. patent application.

When designing and making convenience kits according to instant inventions disclosed herein, the following object should be kept in mind: "It is a principle object to provide a convenience kit which can be used to compound a medical preparation within an open and uncontrolled environment without preparation fluid contamination exterior to the convenience kit and with full assurance of maintenance of a sterile state of product disposed within the convenience kit." The following descriptions provide instructive support for making and using convenience kits which assure meeting that objective.

Generally, convenience kits made and used according to present inventions comprise two sub-kits. An example of such a convenience kit 10 is provided in FIG. 1 wherein an exterior sub-kit 20 is securely affixed to a plastic bag 30, being a primary part of a protectively enclosing sub-kit 32 via a bag entry technology (in this example a BEST filter assembly 40.) In this example, a prefilled and sterilized IV container 43 is disposed for receiving a compounded medicine additive via BEST filter assembly 40 as compounded using exterior sub-kit 20 with no exposure of fluid of any kind being displaced from containment through compounding and communicating compounded medicine into a receiving container, such as container 43.

Because each convenience kit, made and used according to the instant inventions disclosed herein, is used but once, various specialized kits can be tailored to meet special and particular requirements of each type of medical preparation, as desired. As an example, such a preparation can be measured, compounded, sterilized and communicated to a container, such as container 43, through an entirely closed pathway, which is a characteristic object of all kits made according to the instant inventions disclosed herein.

More than one mode of sterilizing, which should be used if such can be used without effective medicine degradation, can be applied, within the scope of invention disclosed herein. There are cases when no sterilization should be performed on a medicine due to such effecting medicinal degradation or the integral nature of the medicine, itself, such as medicine which is so lethal by its very nature that no further sterilization is required. As disclosed hereafter, convenience kits can be made and used within the scope of inventions disclosed herein for a vast number of medicine compounding applications.

Sterilization, when provided, is accomplished prior to preparation entry into an enclosing sub-kit, such as enveloping sub-kit 32. As disclosed hereafter, sterilization can be effectively accomplished using filtering or light sterilization. The fluid communicating interface provided by bag entry technology assembly being within the scope of the present inventions can be varied to meet sterilizing requirements for each preparation receiving kit, such as convenience kit 10.

Figure 2:
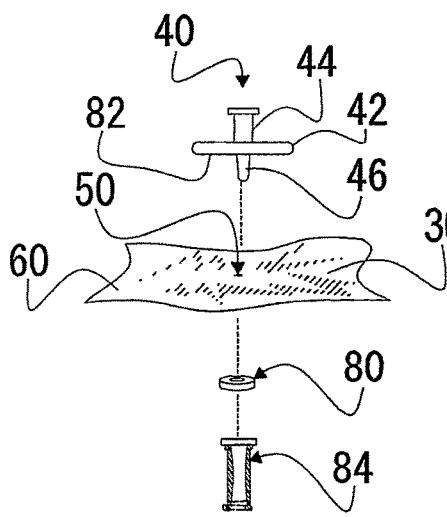
FIG. 2 is an exploded view of parts for a BEST assembly with parts aligned for assembly.
Figure 3:
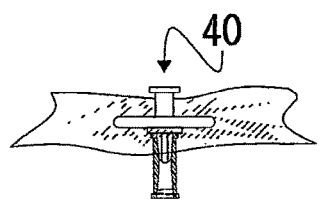
FIG. 3 is a schematic diagram of parts seen in FIG. 2 assembled.

Based upon character and need of medicine being compounded, a given bag entry technology interface can also be variably used. An exploded view of one such interface is a PRIOR ART bag entry technology, i.e. BEST 40, as seen in FIGS. 2-3 which discloses a medical grade filter 42, preferably 0.2 micron rating or better, which comprises a female fitting 44 for receiving fluid to be sterilized and an opposing male tapered fitting 46 which can be inserted through a pin-hole 50 previously prepared in a plastic bag 30 (of which only a portion 60) is seen. The bag 30, being sized and shaped of material selected for clarity and pliancy, when closed and sealed provides a complete enclosure for items disposed inside.

A gasket 80 and a luer female/female luer component 84 which has a female luer fitting 84 for securely engaging tapered fitting 46 without spillage of liquid or release of gas. Gasket 80 is preferably made of incompressible but malleable material such as silicone and, being cylindrically in shape, is sized to fit tightly about fitting 46 to provide for complete fluid containment when disposed against bag material at portion 60 of bag 30 about pinhole 50 and being compressed against a facing planar filter housing 82 to make an effective seal against fluid flow. Female/female fitting 84 and male tapered fitting 46 are preferably securely affixed together by adhesive to assure the resulting BEST 10 is continuously effective. An assembled example of BEST 40 is seen assembled in FIG. 3.

Figures 4, 6:
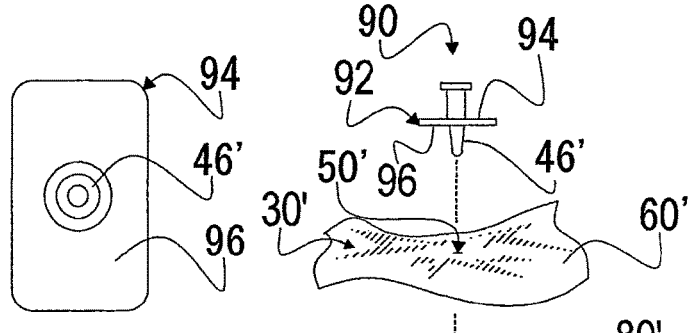
FIG. 4 is an exploded view of parts for a BET assembly with parts aligned for assembly.
FIG. 6 is a front elevation of a male/female connector seen in FIG. 4 wherein a planar plastic bag surface surrounds a protruding male fitting.
Figure 5:
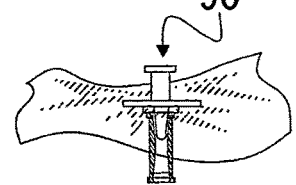
FIG. 5 is a schematic diagram of parts seen in FIG. 4 assembled.

Reference is now made to FIG. 4 wherein an exploded view of another form of bag entry technology, BET 90, is seen. Note that a tapered fitting 46' is a part of a male/female luer connector 92. Connector 92 comprises a flange construction 94, having a flat, planar bag-facing surface 96, best seen in FIG. 6, and a tapered male fitting 46' which can be inserted through a pinhole 50' previously prepared in a plastic bag 30' (of which only a portion 60' is seen as provided for clarity without need for viewing an entire plastic bag). A gasket 80' and a female/female component 84 which has a female luer fitting 84 for securely engaging tapered fitting 46' without spillage of liquid or release of gas. Gaskets 80 and 80', as stated supra, are preferably made of cylindrical, incompressible but malleable material such as silicone tubing and sized and shaped to provide for complete fluid containment when disposed against bag material about pinholes 50 and 50' and being compressed against a facing planar surface such as bag-facing surface 96 to make an effective seal against fluid flow. Female fitting 84 and tapered fitting 46' are preferably securely affixed together by adhesive to assure the resulting BET 90 is continuously effective. A fully constructed example of BET 90 is seen in FIG. 5. An example of a commercial fitting which can be used for male/female luer connector 92 is Qosina Corporation Female Lure Lock Connector part number 96, Referring once more to FIG. 1, which is an exemplary convenience kit 10, as provided, for displacing a prescription of a compounded medicine prepared using exterior sub-kit 20 into a prefilled (and sterilized) IV Bag 43 of enclosing sub-kit 32. Note that, to assure sterile preservation and fluid retention, convenience kit 10, as is true of kits made according to the inventive disclosure disclosed herein, is provided assembled, as seen in FIG. 1. In this case, medicine to be compounded can be drawn using vials disposed in vial adapters numbered 110, 110' and 110".

Particularly, vials are not shown in FIG. 1, and not necessarily provided as part of a delivered kit, as they are selected by the user and dependent upon prescribed medicines and therefore not generally provided as part of convenience kit 10. The medication containing vials are not generally supplied with convenience kit 10 due to vast variation in patient prescriptions. Vial adapters 110, 110' and 110" are seen affixed to a manifold 112 for raw medicine communication. Manifold 112 is seen to comprise three manually switchable valves 120, 120' and 120" whereby, as one who is skilled in manifold art understands, each vial can be accessed individually. It also should be recognized that the number of vials and valves in each manifold can be varied within the scope of inventions disclosed herein. The number of vials are generally defined by compounding needs of a particular convenience kit application and provided therefore.

Generally, displacement of medicines from vials is provided by a syringe measurement assembly, such as TMD syringe assembly 140. Note that in the TMD syringe assembly 140, syringe 150 is totally enclosed and sealed within a plastic bag 152. Syringe 150 communicates with through a tubing tether 158 via a BET assembly 154. It should also be noted that bag 152 has sufficient length and girth for permitting displacement of a plunger rod 156 of syringe 150 by digital contact only through the exterior of bag 152. Micro-tubing tether 158 is securely affixed between BET assembly 154 and manifold 112 thereby providing for displacing syringe 150 to be displaced spout up for gas delivery a spout down for liquid delivery without displacing other convenience kit 10 items, such as manifold 112.

Tethered measurement and delivery syringe (TMD 150) communicates, in this example, individually with the plurality of vial adapters generally numbered 110, 110' and 110" via pathway 122 internal to manifold 112 as controlled by valve 130 and other valves numbered 120, 120' and 120"

disposed within manifold 112. Note that fluid flow pathway 122 is fully contained from end to end of manifold 112 and fluid only communicates along pathway 122 between filter 40 and tethered syringe 150 and each vial 110, 110' and 110" and with a second source syringe 134, via a second tether 162, as individually permitted by manifold 112 switching. In other words, all fluid communication within exterior sub-kit 20 is along a closed but variably accessed fluid flow path 122. Note again that tether 158 is permissive for syringe 150 to be rotated for differentiation of delivery of either gas or liquid and/or vibrated for mixing of compounded medicine without affecting medication source vessels affixed to manifold 112. For similar reasons, a TFP syringe 134 is also affixed to manifold 112 via a tether 162.

Figure 13:
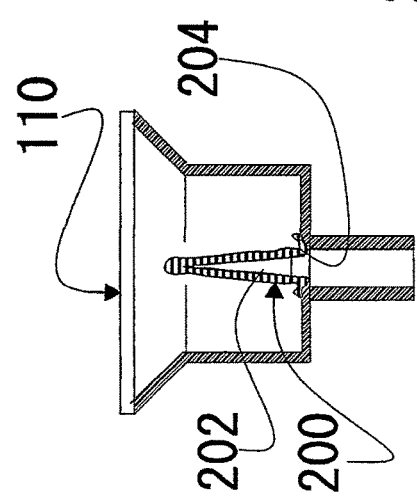
FIG. 13 is a schematic diagram cross section of the vial adapter seen in FIG. 12, but with a vial spike valve affixed about a vial septum piercing spike of the conventional vial adapter seen in FIG. 12.
Figure 12:
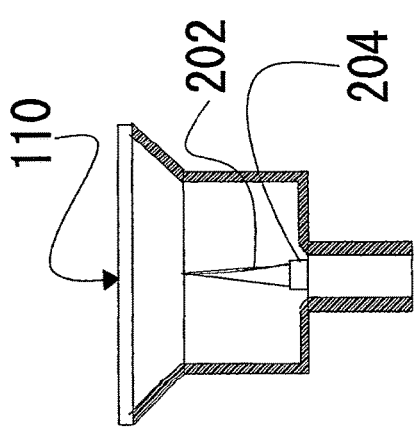
FIG. 12 is a schematic diagram cross section of a conventional vial adapter.

As an open vial adapter spike can provide unimpeded flow of liquid from pathway 122 to find opportunity to escape into the surrounding environment due to an inadvertent error in switching a manifold 112 valve, it is imperative, for user and product safety, to provide each vial adapter with a normally closed valve which is only opened when a vial is spiked and thereby remaining closed by being affixed to manifold 112, to communicate only with pathway 122, to further assure containment of all fluids in exterior sub-kit 20. Such can be provided by use of currently available male/female connectors as one who is skilled in the art of hazardous drug preparation would understand, but use of such connectors increases convenience kit cost and results in a larger than desired exterior sub-kit size and volume along with a greater than desired medicine holding dead space. For this reason, it is recommended that a spiking-actuated, normally closed vial spike valve 200 be affixed about a vial spike 202 of a vial 201, as seen in FIG. 13. For reference, a vail adapter 110 is seen unattached in FIG. 12 with a bare spike 202 disposed above a cylindrical base part 204. Note, bare spike 202 is a commonly provided state for current conventional vial adapters. Such spikes are now commonly protected with sterility maintained by vial adapter packaging, but once the packaging is removed, each such spike is subject to being contaminated.

Figure 14:
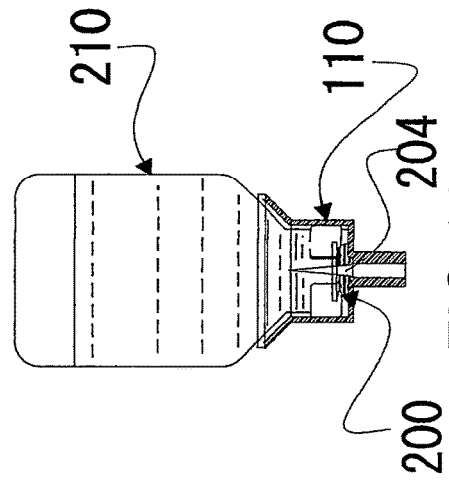
FIG. 14 is a schematic diagram of a vial with septum spiked by the spike seen in FIG. 12 and the vial spike valve being opened and compressed below the vial septum.

As seen in FIG. 13, a vial adapter spike valve 200 is affixed about a spike 202 and anchored about an inferior portion 204 of spike 202 to assure containment of any fluid flow from an associated fluid pathway before a vial is affixed thereto. Similar to a blood valve, used with blood accessing vacuum tubes, spike valve 200 is opened upon spiking of a valve septum by a vial spike 202. As seen in FIG. 14 vial adapter spike valve 200 is sized and shaped to be trapped below the septum of the vial to form a fluid flow impeding gasket.

Component Selection

In general, all connecting components should be tested and certified for each particular use. As an example, intra-connecting fittings should be certified to be leak proof and wherever possible securely affixed to assure absolute fluid containment. Of course, a limited number of components will have to be connected and disconnected as a necessary process in vessel filling and handling. For such purposes, connectors generally identified as "dripless connectors" should be used, and, whenever possible, flushing with a clearing solution, such as normal saline, should be employed for increased safety when detaching connections.

Sterilizing filters should only be used when prescribed medicine performance is not affected by sterilizing filtration. If sterilizing filters cannot be used, light sterilization can be considered. However, unlike filter sterilization, light sterilization, even when applicable for use, must be used with knowledge and care. In the case of light sterilization, one state of use does not fit all. Contact with medicine manufacturer is recommended before performing any light-based sterilization. When employing gas (air), gas entry should be controlled with only sterilized gas provided as required and a one-way valve should be used to assure only fluid flow is permitted into the site of use.

Figure 9:
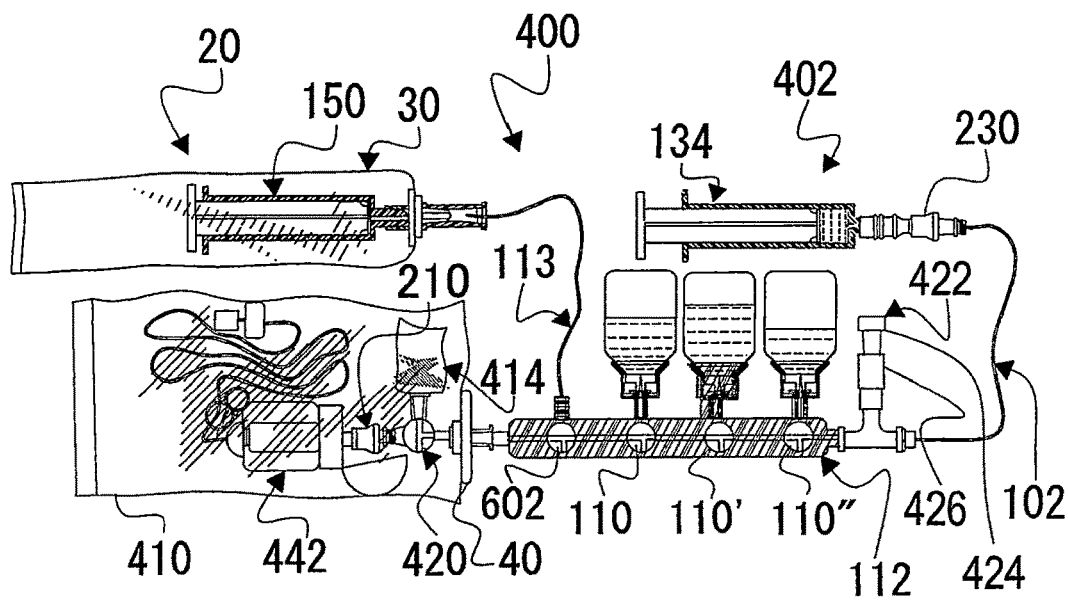
FIG. 9 is a schematic diagram which is similar to the diagram seen in FIG. 8, but being fitted with an elastomeric ball container and a greater number of devices affixed to an exterior sub-kit.
Figure 10:
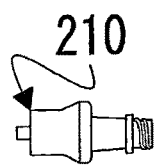
FIG. 10 is a schematic diagram of A dripless connector having the form of a connector known by CLAVE® which is designed as a female connector which is dripless and made and sold by ICU Medical, Inc.
Figure 10A:
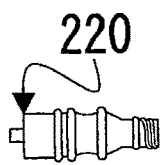
FIG. 10A is a schematic diagram of dripless a connector having the form of a connector referenced as SPIROS® which is also made and sold by ICU Medical, Inc.
Figure 10B:
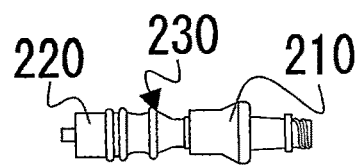
FIG. 10B is a schematic diagram of the components seen FIGS. 10A and 10B joined to form a separable dripless connector.

Following is a list of components with recommendations for considerations for use:

1. CLAVE, seen in FIG. 10, (made by ICU Medical, Inc.) is an example of a female luer fitting valve which is currently in common use with hazardous drugs. A symbol for a Clave component 210 is seen in FIG. 10.
2. SPIROS, seen in FIG. 10A, (made by ICU Medical, Inc.) is an example of a male luer fitting valve which is currently in common use with hazardous drugs. A symbol for a Spiros component 220 is seen in FIG. 10A.
3. When there is a requirement for a detachable connection, it is recommended that a combination like a CLAVE and a SPIROS be affixed one to the other to operate as a single component 230 when attached, as seen in FIG. 10B.
4. . . . . Gas sterilization can be provided by commercial gas membrane filters generally provided in female luer fittings. Another filter called a Pasteur Filter and based upon passage of air through a series of gas velocity reducing, sterilizing chambers can also be used. A symbol for an air sterilizing filter 232 is seen in FIG. 9.
5. A one-way valve 424, used for assuring no escape of matter from a fitting which communicates with an exterior environment, is also seen in FIG. 9.
6. Manifolds, such as, by example, manifold 112, which is seen in FIGS. 1 and 8, are components specifically designed for fluid containment while providing for manually selectable access to predetermined fluid pathways are commonly available commercially.

Various examples of different types of enveloping sub-kits and exterior sub-kits made and used for safety in compounding various hazardous medicine prescriptions are seen in FIGS. 1, 8, 9 and 11. It should be kept in mind that, in all such types of convenience kits, primary objects are to maintain all fluids in their entirety, within each enveloping and exterior sub-kit (and within all fluid communications therebetween).

Figure 8:
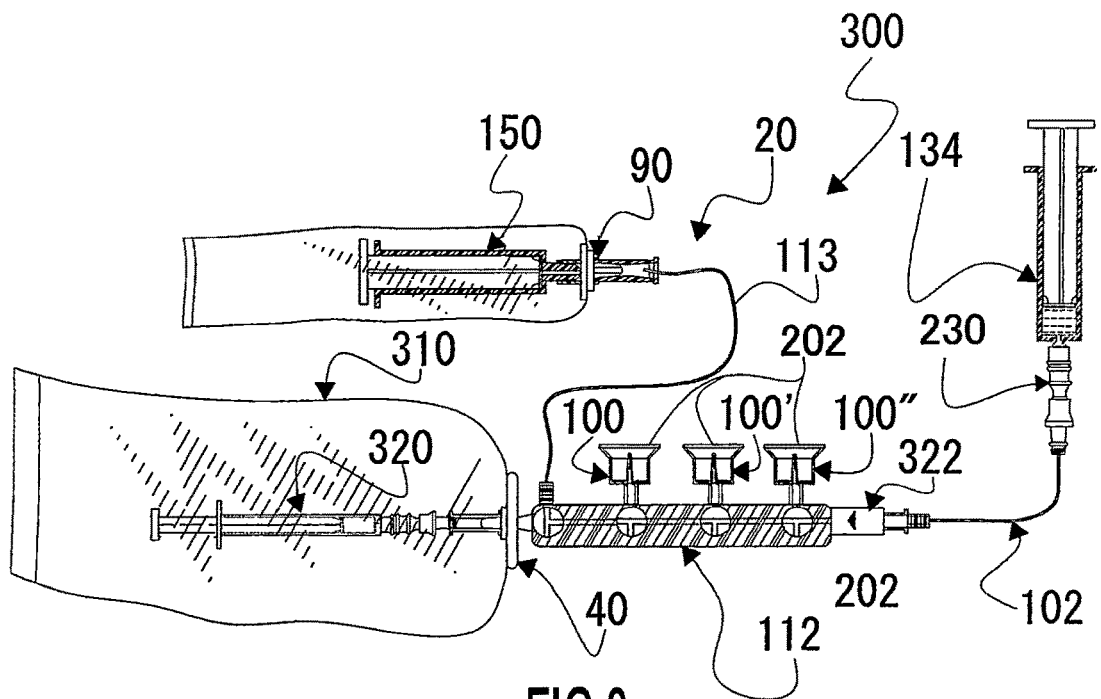
FIG. 8 is a schematic diagram which is similar to the diagram seen in FIG. 1, but with a single syringe disposed as a receiving container in an enclosing sub-kit.

Convenience Kit 10 seen in FIG. 1, and described supra, is a rudimentary kit which uses a TFP syringe 134 for communicating gas (air) and flush liquids to manifold 112. The receiving vessel is an IV bag 43 in enclosing sub-kit 32. The many effective forms of convenience kits made according to the inventions disclosed herein are exemplified by the following additional examples:

A convenience kit 300 is seen in FIG. 8. An exterior sub-kit 20 is securely affixed to an enclosing sub-kit 310 via a sterilizing filter 40. A TFP syringe 134 is affixed to manifold 112 by means of a securely affixed CLAVE/SPIROS combination 230 which assures no matter flow when TFP syringe 134 is detached for filling, as an example. Exterior sub-kit 20 is seen to further comprise vial adapters 110, 110' and 110". Each vial adapter spike 202 is covered and protected by a vial adapter spike valve 202, as seen in FIG. 13 (each such vial adapter being affixed to a manifold 112). Pathway variations associated with manifold 112 use are disclosed in FIGS. 15-19A, hereafter. Note that all fluid pathways are closed to communication with the exterior environment.

A more sophisticated version of a convenience kit made according to the instant inventions disclosed herein is seen as convenience kit 400 in FIG. 9. To fulfill the requirements of maintaining all matter enclosed while compounding, the only separable part is a TFC syringe 134 which communicates with other parts of exterior sub-kit 402 via a combination CLAVE/SPIROS component 230 (as seen in FIG. 10B), which permits TFC syringe 134 to be separated for fluid filling in compounding processes requiring an influx of gas (air) or liquid (such as normal saline) without communicating fluid resident in manifold 112 into the environment external to exterior sub-kit 402. To reduce the number of steps required for introducing gas through manifold 112 to TMD syringe 150 for such activity as performing a bubble test on filter 40, an air filtering assembly 422 is provided in direct communication with manifold 112. As seen in FIG. 9 air filtering assembly 422 comprises a sterile filtering part 424 and a one-way valve 426. Both parts 424 and 426 are commonly commercially available. With filtering assembly 422 in place, sterile gas (air) can be drawn into TMD syringe 150 by simple manipulation of the TMD syringe 150 plunger piston 156 from outside bag 30. The receiving vessel of enclosing sub-kit 410 is an elastomeric ball 442. A CLAVE 210 is affixed to communicate with BEST filter assembly 40 and thereby provide for a dripless parting connection. Note that TMD syringe 150, being entirely enclosed in a plastic bag to assure all fluid containment, communicates with tether 113 via a BEST assembly 40 which is securely affixed to manifold 112. Exemplary steps for using convenience kit 400 is disclosed hereafter in disclosure referencing FIGS. 20-35.

Figure 11:
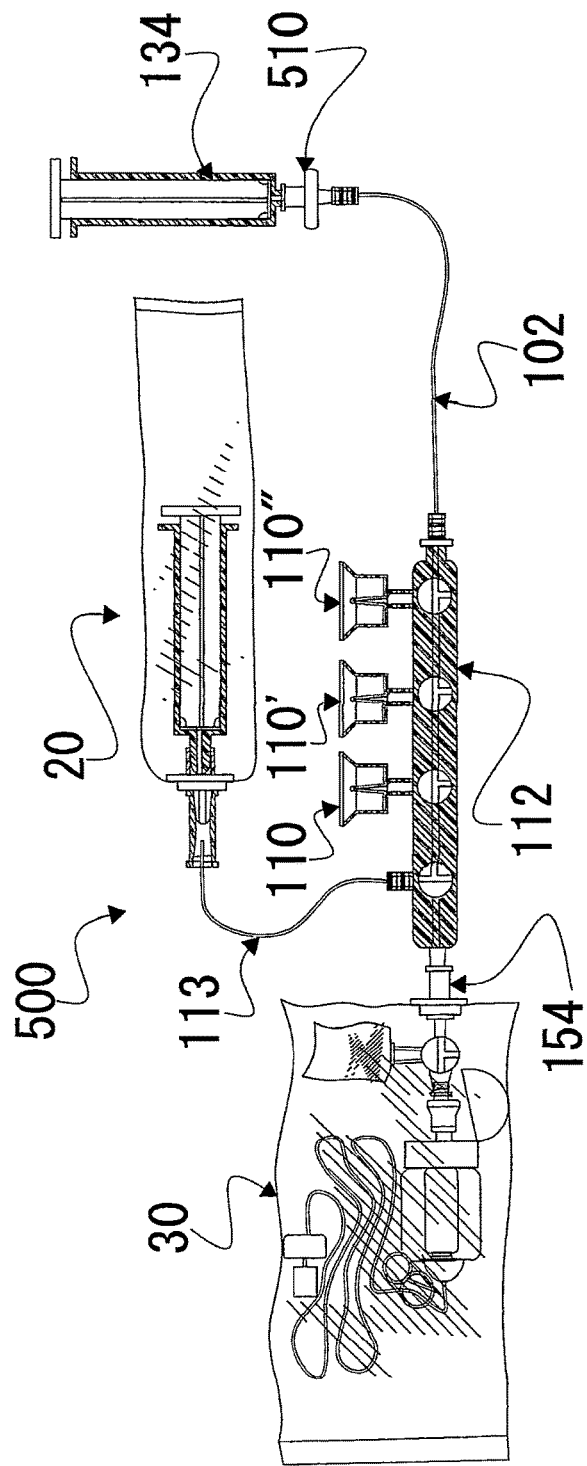
FIG. 11 is a schematic diagram of a side elevation of a convenience kit comprising an enclosing sub-kit securely affixed via BET to an exterior sub-kit made according to instant inventions with an elastomeric ball disposed as a single receiving vessel.

Another example is a convenience kit made according to the instant inventions which is disclosed herein in FIG. 11 as convenience kit 500 for compounding medicine which cannot be sterilized using a sterilizing grade filter. Recalling that, even though medicine is not sterilized as part of convenience kit 500 function, it is imperative that no activity within convenience kit 500 should degrade sterility of medicine being compounded beyond the simple mixing of medicines of different SALs. In other words, the act of compounding should not increase the overall SAL of the resulting mixture. It should be noted that, in this example, TFP syringe 134 is releasably affixed to a sterilizing filter 510 to assure all matter dispensed from TFP syringe 134 will not effect, inappropriately, sterility of other fluids which will be passed through manifold 112. Filter 510 communicates to manifold 112 via tethering tube 102. Components associated with manifold 112 (i.e. vial adapters 110, 110' and 110" are the same a vial adapters previously cited) and other parts of an exterior sub-kit 20 are as previously disclosed. However, the assembly used for exterior sub-kit 20 to enclosing sub-kit 30 communication, in this example, is a BET assembly 154.

Figure 7:
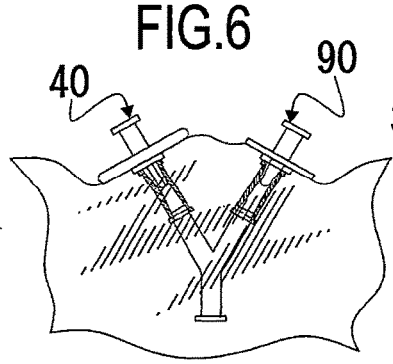
FIG. 7 is an exemplary combination of BET and BEST assemblies being jointly affixed to a single segment of a plastic bag.

As combinations of medicines can include both medicine which can be sterilizing using a medical grade filter and medicine which cannot be so filtered, two exterior sub-kits can be used concurrently by providing both a BEST assembly 40 and a BET assembly 90 affixed to the same enclosing sub-kit bag 30 as seen in FIG. 7. (Of course, each such assembly would be affixed to an individual exterior sub-kit, as numbered by application, as disclosed supra.)

A general method for pathway control within manifold 112 is exemplified in FIGS. 15, 16, 17, 18 and 19. Methods seen and exemplified in FIGS. 15, 16, 17, 18 and 19 and in FIGS. 15A, 16A, 17A, 18 and 19A are provided as an aid for understanding processes for controlling pathways in manifold 112 and do not necessarily exemplify manifold 112 use for compounding action. Note, in this example in FIG. 15, manifold switches 600, 600', 600" and 610 are all in the same state as referenced to associated vial adapters 110, 110', 110" and TMD syringe 150 manifold connection 620, as seen in FIG. 15. For clarity of purpose, vials 604, 604' and 604" are respectively affixed to vial adapters 110, 110' and 110". Valve states for valves 610, 610', 610" and 602 are seen in associated FIGS. 15A, 16A, 17A, 18A and 19A, respectively. As seen in FIG. 15A, pathway 122 is open end to end of manifold 112 for valve states and all valve adapter to valve states are all closed as seen in FIG. 15. Changing states of valves 600 and 602, as seen in FIG. 16 opens a communication pathway in manifold 112 as seen in FIG. 16A. Changing state of valve 600', as seen in FIG. 17 opens a communication pathway in manifold 112 as seen in FIG. 17A. Changing state of valves 600", as seen in FIG. 18 opens a communication pathway in manifold 112 as seen in FIG. 18A, and changing state of valve 602, as seen in FIG. 19 opens a communication pathway in manifold 112 as seen in FIG. 19A. In this last valve state, TMD syringe 150 communicates via tether 113 and valve 602 with a pathway 620 out of manifold 112 as is also seen in FIG. 19A.

As an example, reference is now made to FIGS. 20-35 wherein a plurality of steps for effective use of a convenience kit 400 (also seen in FIG. 9) for acquiring and compounding a prescription of medicine from vials affixed to vial adapters 110, 110' and 110" without communication of any fluid, initially resident in vials affixed to vial adapters 110, 110' and 110", being released into the exterior environment.

Priming

Figure 20:
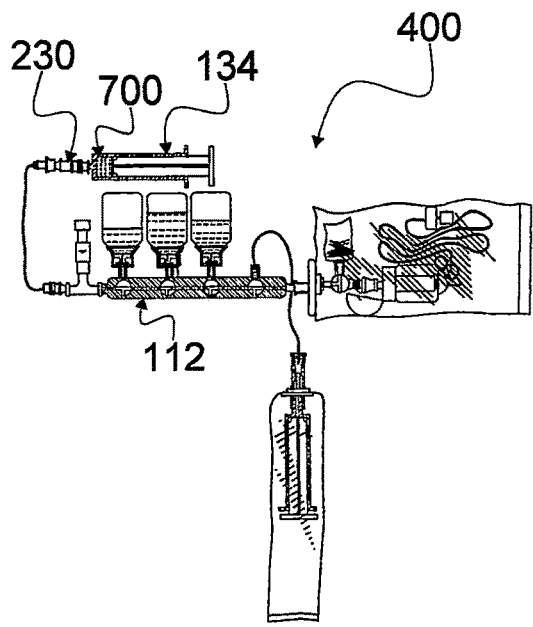
FIG. 20 is a schematic diagram of a convenience kit made and being used according to the instant invention at the beginning of an elastomeric ball filling procedure.

As seen in FIG. 20, a bolus of liquid 700 has been provided in TFP syringe 134 by means well understood and performed by those skilled in syringe processes in hazardous medicine applications. While other methods are readily available, such as using medicine in one of the vials securely affixed to manifold 112, TFP syringe 134 is readily detached by separating CLAVE/SPIROS component 230, which is seen in FIG. 20, before filling TFP syringe 134.

Figure 21:
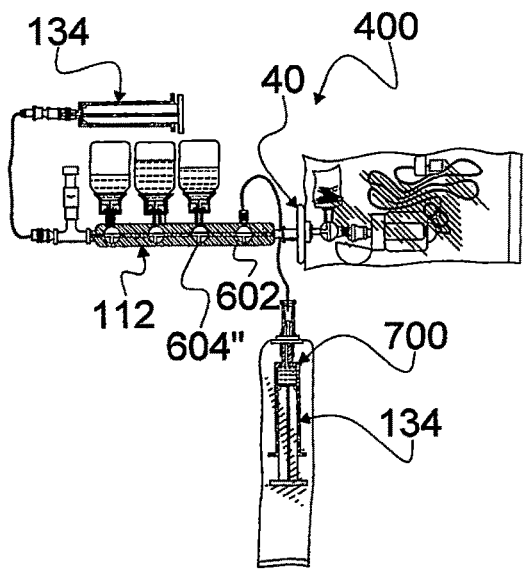
FIG. 21 is a schematic diagram of the convenience kit seen in FIG. 10 with liquid (preferably normal saline) prepared for delivery through a tethered medical syringe for priming a BEST filter.

As seen in FIG. 21, dispensing liquid from TFP syringe 134 dispenses priming liquid 700 directly through manifold 112 and through BEST filter assembly 40 with assurance flushing liquid is sterilized as are all fluids which are dispensed through BEST filter assembly 40. With BEST filter assembly 40 primed, convenience kit 400 is ready for compounding. 15

Compounding

Figure 22:
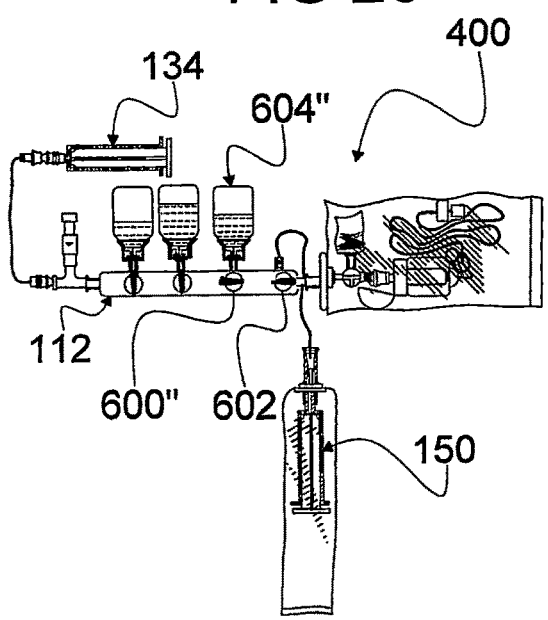
FIG. 22 is a schematic diagram similar to FIG. 21 wherein the liquid has been delivered to prime the filter.
Figure 23:
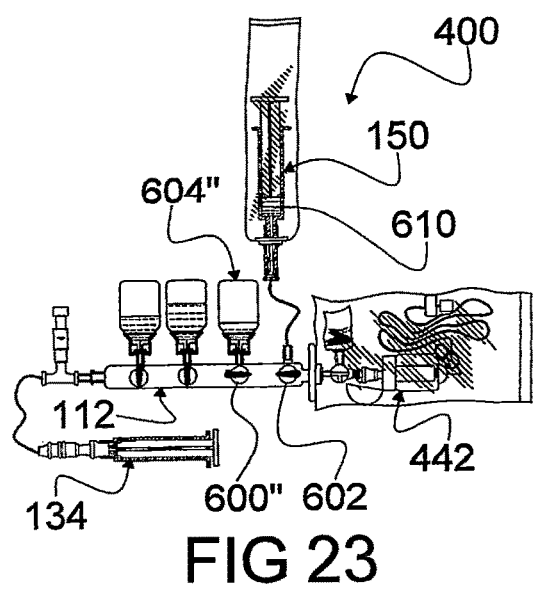
FIG. 23 is a schematic diagram similar to FIG. 22 with manifold valves set for drawing raw medicine from a specific vial.
Figure 24:
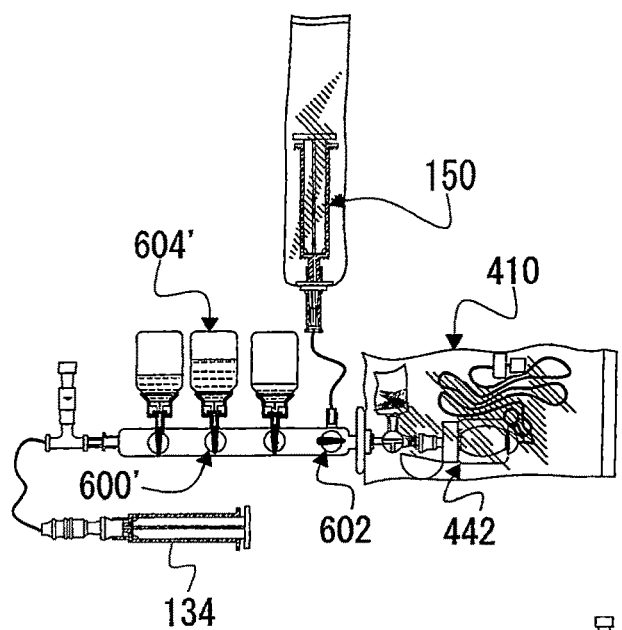
FIG. 24 is a schematic diagram of the convenience kit seen in FIG. 23 with raw medicine drawn according to FIG. 23 dispensed through BEST assembly into an elastomeric ball.

As seen in FIG. 22, valves 600" and 602 are rotated to provide a manifold 112 fluid pathway between vial 604" and TMD syringe 150. As seen in FIG. 23, a prescribed volume of medicine 610 has been drawn from vial 604" into TMD syringe 150. As seen in FIG. 24, volume of medicine 610 has been dispensed (into elastomeric ball 442; note valve 600" is rotated to a closed state and valve 602 is rotated to provide a communicating pathway whereby medicine 630 (see FIG. 23) is dispensed into elastomeric ball 442 which is disposed within enclosing sub-kit 410.

Figure 25:
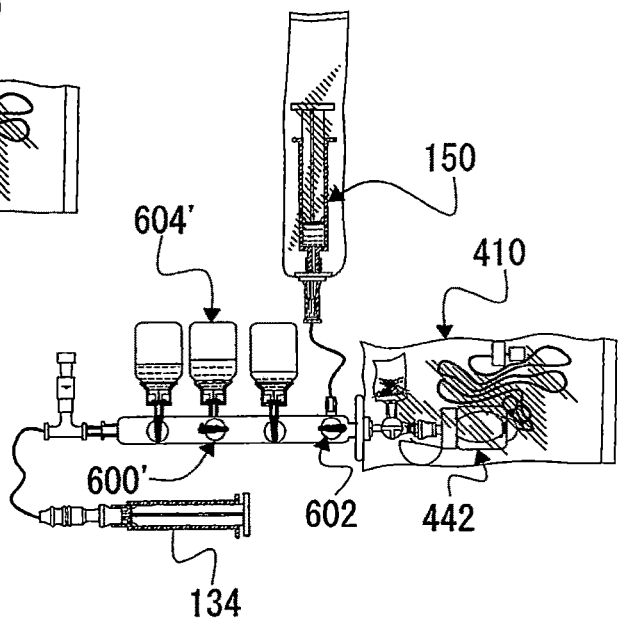
FIG. 25 is a schematic diagram similar to FIG. 24 with manifold valves set for drawing raw medicine from a second vial.

As seen in FIG. 25 valve 600' and valve 602 are rotated to permit medicine 610' to be drawing from vial 604' into TMD syringe 150.

Figure 26:
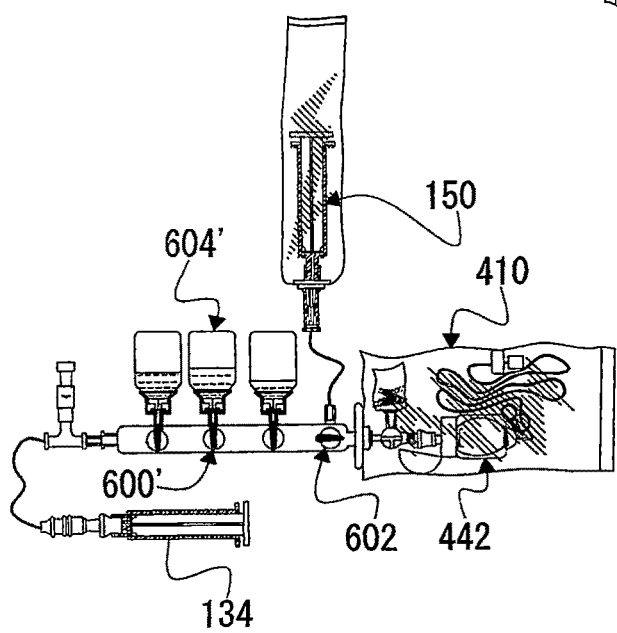
FIG. 26 is a schematic diagram of the convenience kit similar to the configuration seen in FIG. 25 with valve switches set for communicating raw medicine into the elastomeric ball.

As seen in FIG. 26 valve is rotated to a closed state and valve 602 is rotated to permit dispensing of medicine 610' (unseen) into elastomeric ball 442.

Figure 27:
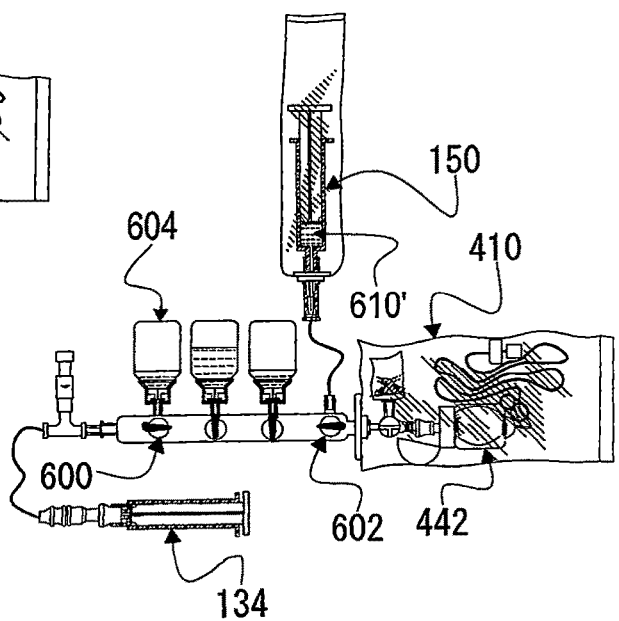
FIG. 27 is a schematic diagram of the convenience kit seen in FIG. 26 with valve switches set and medicine drawn from a third vial.
Figure 28:
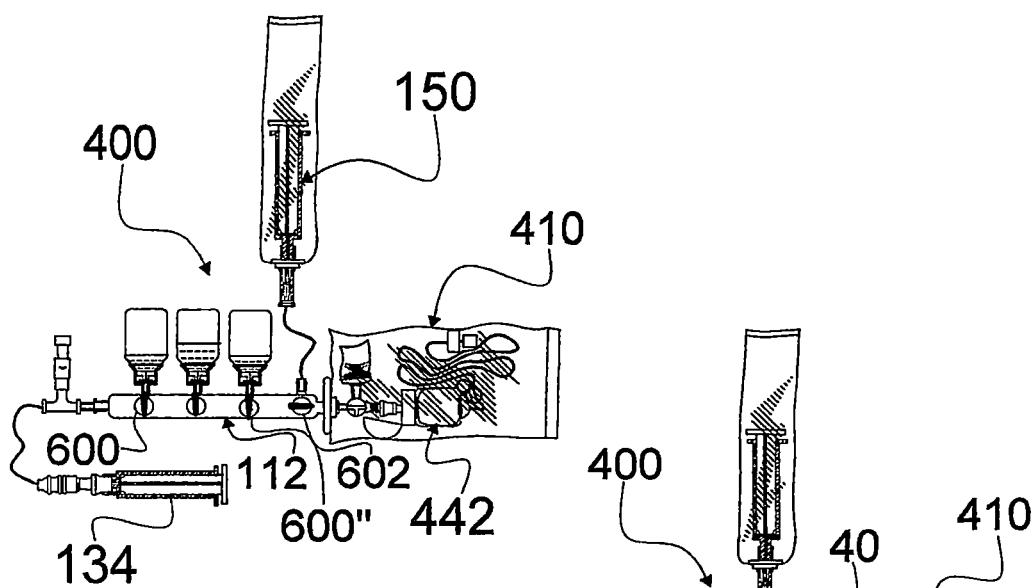
FIG. 28 is a schematic diagram of the convenience kit seen in FIG. 27 with valve switches set for delivering raw medicine delivered through the BEST assembly into the elastomeric ball.

As seen in FIG. 27, valves 600 and 602 are rotated to provide a manifold 112 fluid pathway between vial 604 and TMD syringe 150. Also seen in FIG. 27, a prescribed volume of medicine 610" is drawn from vial 604 into TMD syringe 150. As seen in FIG. 28, syringe 150 is cleared of volume of medicine 610" which has been dispensed into elastomeric ball 442, valve 600" is rotated to a closed state and valve 602 is now rotated to provide a communicating pathway whereby medicine 630 (not shown) is dispensed into elastomeric ball 442 being disposed within enclosing sub-kit 410.

Flushing

Figure 29:
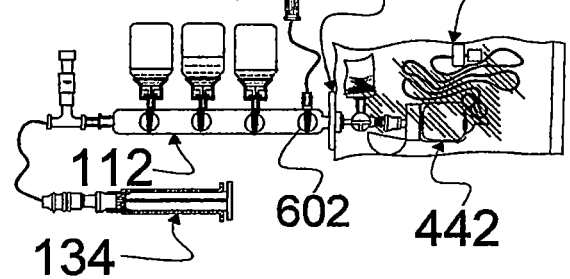
FIG. 29 is a schematic diagram of the convenience kit seen in FIG. 28 with valve switches set, as seen in FIG. 14A, in position to allow a pathway for fluid delivery from a tethered fluid source syringe.
Figure 30:
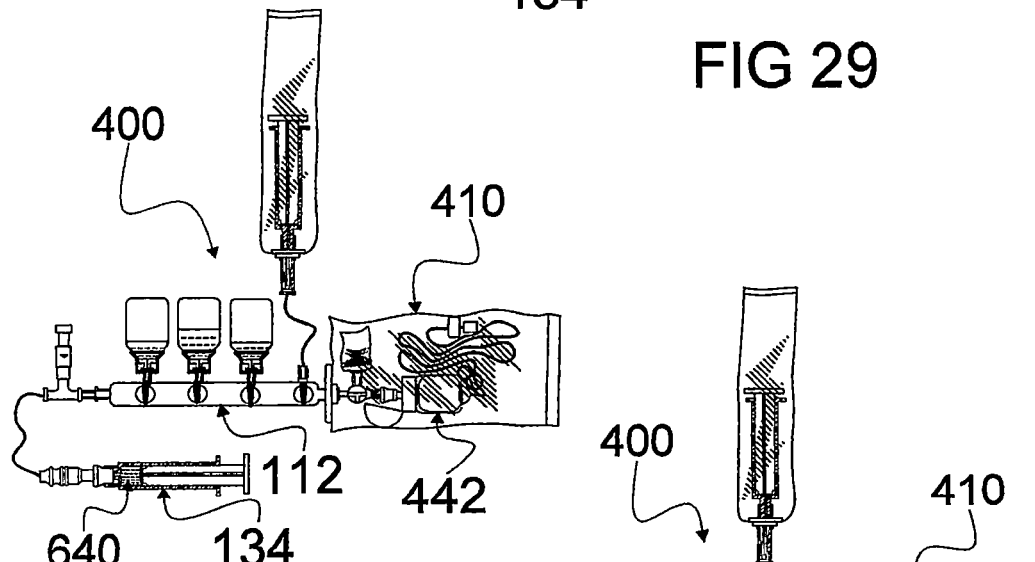
FIG. 30 is a schematic diagram of the convenience kit seen in FIG. 29 with valve switches set in position to form a pathway, as seen in FIG. 14A, for fluid delivery from a tethered fluid source syringe directly to the BEST assembly.
Figure 31:
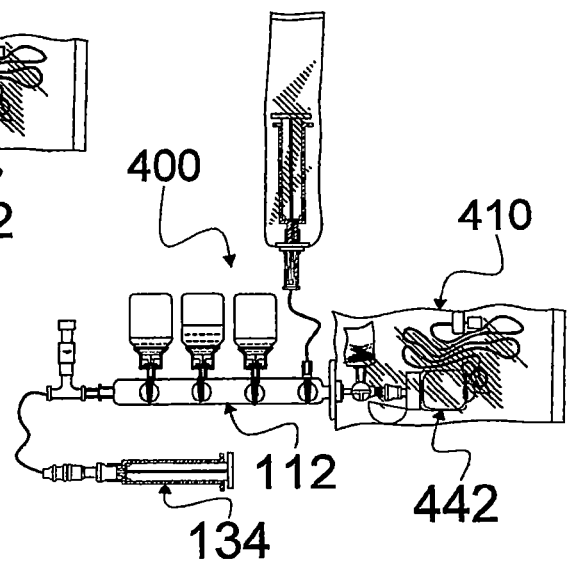
FIG. 31 is a schematic diagram of the convenience kit seen FIG. 30 with a flushing solution dispensed from the tethered fluid source syringe through the BEST assembly and to the elastomeric ball to provide for a flushed interconnection between the BEST assembly and the elastomeric ball.

As seen in FIG. 29, valve 602 is rotated to provide an open pathway from TFP syringe 134 through filter assembly 40 into enclosing sub-kit 410. In FIG. 30, TFP syringe 134 is seen provided with a flush solution 640. As those who are skilled in IV applications understand, it is common practice to flush a line connection before disengaging the connection to reduce likelihood of undesirable contamination. TFP syringe 134 is seen emptied in FIG. 31, having delivered flush solution 640 (not seen in FIG. 31) preparatory to disengaging elastomeric ball 442 for use in a medical treatment.

Testing Filter Efficacy

Figure 33:
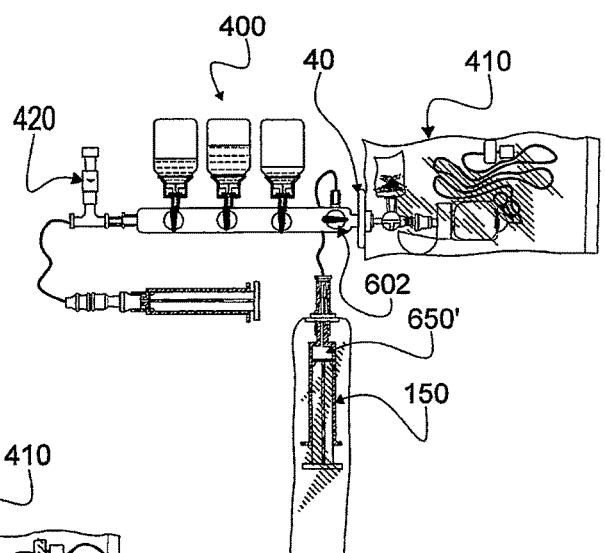
FIG. 33 is a schematic diagram of the convenience kit seen with a partial delivery of the volume of air remaining in the tethered medical syringe seen in FIG. 32 being an indicative of efficacy (acceptable operation) of the BEST filter.

However, should filter assembly 40 have failed for any reason, compounded medicine in elastomeric ball should not be used. For this reason, a final filter efficacy test (a bubble test) should be performed. Valve 602 is rotated (see FIG. 33) to provide access by TMD syringe 150 to a pathway through manifold 112 to air filtering assembly 420, from which a bolus of air 650 is seen drawn into TMD syringe 150. In FIG. 33 bolus of air 650' is seen diminished, but not fully dispensed, as an indication that filter assembly 40 has passed the filter test by being occluded to passage of gas.

Accessing Filled Product

Figure 34:
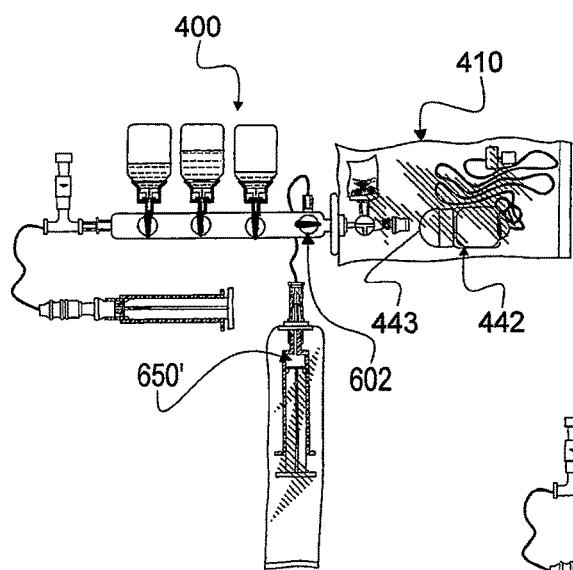
FIG. 34 is a schematic diagram of the convenience kit seen in FIG. 33 with the elastomeric ball in the enclosed kit capped and detached.
Figure 35:
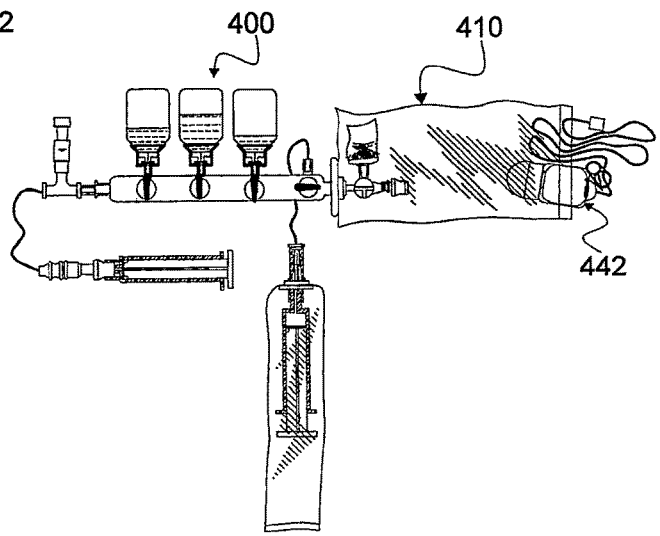
FIG. 35 is a schematic diagram of the convenience kit seen in FIG. 33 with the plastic bag of the enclosing sub-kit opened permissive to accessing the elastomeric ball for use in a medical procedure.

Before a product is accessed from an enclosing sub-kit, each such filled kit should be capped to assure retention of both fluid and sterility. As seen in FIG. 34 an enclosed elastomeric ball 442 hinged cap 443 has been rotated and closed preparatory to accessing elastomeric ball from enclosing sub-kit 410. As seen in FIG. 35, filled elastomeric ball 442 is seen being dispatched from enclosing sub-kit 410 for use.

Figure 36:
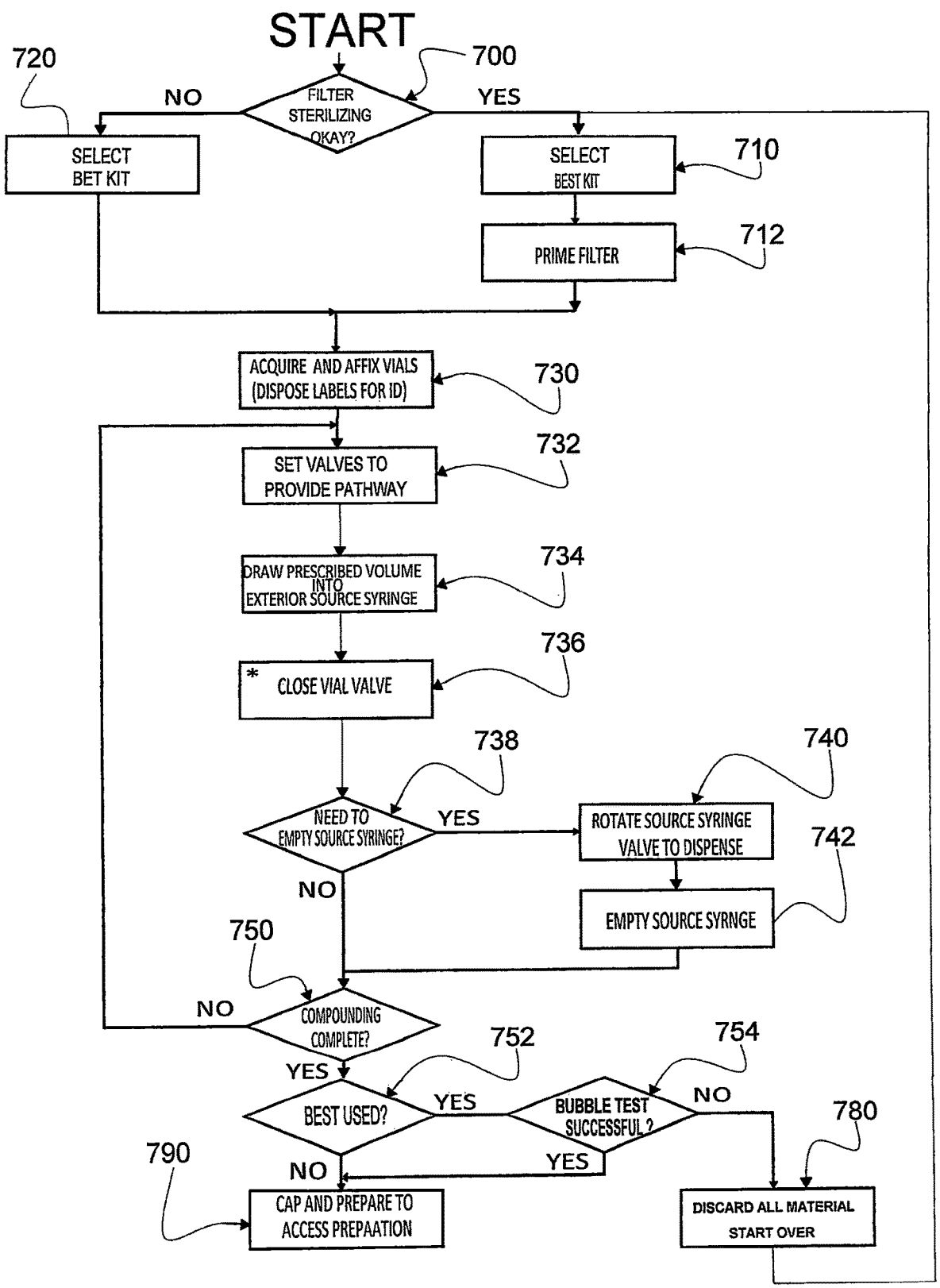
FIG. 36 is a flow diagram disclosing method of use of convenience kits made according to the instant inventions.

Steps for Convenience Kit Use:

Reference is now made to a FLOW CHART seen in FIG. 36 (from which references to FIGS. 20-35 are made) wherein examples of steps used for using convenience kits made according to the present inventions are provided. A first step as seen in decision block 700 of FIG. 35 is used for determining which convenience kit, made according to the instant inventions disclosed herein, should be selected for use. If medicines provided in vials to be affixed to manifold 112 (as seen in FIG. 22) can be sterilized by filtering, the next step is selecting a kit which provides filtering via BEST technology as stipulated in function box 710. Before accessing medicine from attached vials, the associated filter should be primed as stated in function box 712, and disclosed in FIGS. 21 and 22, If any medicine provided in vials to be affixed to manifold 112 should not be sterilized by filtering, function box 720 which instructs selecting a BET technology based kit (made according to the present inventions). Note that once a convenience kit has been selected, processing steps for medicines to be sterilized and medicines not to be sterilized are the same steps. Prescribed medicine in vials are next affixed to vial adapters as seen, for example, in FIG. 20 per instruction in function block 730.

Adjust manifold 112 valves to select desire fluid pathway for drawing medicine from a preselected vial as instructed in function box 732. Draw prescribed dose into TMD syringe 150, as instructed in function block 734, for example, see FIG. 28. Close fluid pathway from select vial to manifold 112 to stop all flow from the selected vial. If TMD syringe needs to be emptied before proceeding, follow instruction of decision block proceed to function blocks 740 and 742. As instructed in function block 740, rotate valve associated with TMD syringe 150 to provide a flow path into enclosing sub-kit 410, as seen in FIG. 28. Dispense contents of TMD syringe 150 as instructed in function block 742.

Figure 32:
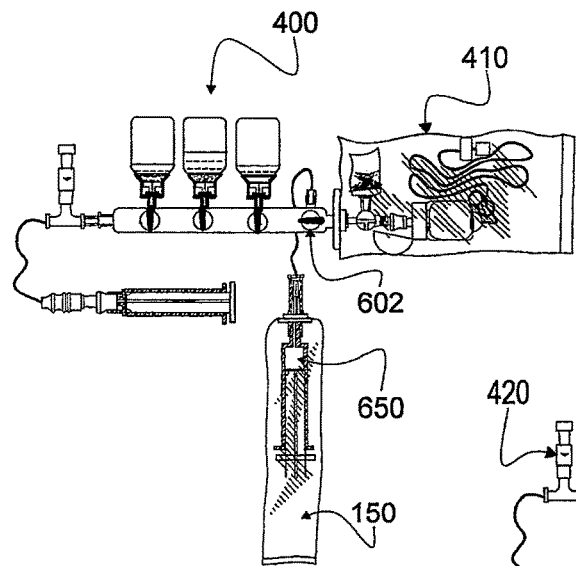
FIG. 32 is a schematic diagram of the convenience kit seen in FIG. 28 with the tethered medical syringe rotated for accessing and delivery of sterilized air into the attached enclosing sub-kit via the BEST assembly.

Decision block 750 determines whether or not compounding is complete. If not, proceed to function block 732. If compounding is complete and a BEST fitted convenience kit is being used, decision block 754 instructs performing a bubble test as seen in FIGS. 32 and 33. If bubble test is unsuccessful, proceed to function block 780 which instructs discarding the entire convenience kit being so used (according to institutional protocol) and proceed to decision block 710 to begin again. Otherwise, proceed to function block 790 from either decision block 752 or 754 to cap the receiving vessel to assure complete closure and then access patient ready vessel as seen in FIG. 35.

Products Provided Sterile Both Inside and Outside:

Yet, another example of uniquely qualified products which can be provided in state and quality, not commonly currently available from compounding, but realizable from kits made according to the instant inventions disclosed herein, is seen, by example, in FIGS. 37-41. An enclosing sub-kit 800 seen in FIG. 37 is seen unattached to an exterior sub-kit, such as exterior sub-kit 20 seen in FIG. 8. However, this, being an example of an enclosing sub-kit, should be understood should always be provided securely affixed to an enclosing sub-kit.

As seen in FIG. 37, a receiving vessel, in the form of a medical syringe 810 is disposed in an inner bag 820 which totally resides within an enclosing sub-kit bag 30. As specified supra, enclosing sub-kit bag 30 communicates only via a BEST filter assembly 90 which is provided securely affixed securely affixed, though not shown in FIG. 37, to an exterior sub-kit, such as exterior sub-kit 302, seen in FIG. 8. Note that the assembly of enclosing sub-kit involves both BEST components as well as BET components. Being provided sterilized, enclosing sub-kit bag 30 retains inner sterility by only receiving sterilized matter through filter assembly 90. As there is no need for further sterilization of matter dispensed into syringe 810, BET 154 components (see FIG. 11), directly affixed to BEST 90 components, provide adequate communicating means for assuring a totally sterile product including inside inner bag 820.

Note also, it is recommended that medical syringe 410 has a CLAVE 210 affixed thereto for dripless detachment from BET 154. To assure retention of matter within inner bag 820, a cap 822 is provided to be affixed to BET 154 to close and seal inner bag 810 before being accessed from outer bag 30.

Medical syringe 810 is seen filled in FIG. 38. Due to use of luer fitting connections, more than one medical syringe 810 can be filled within enclosing sub-kit bag 30, as seen in FIG. 39. Note also that a cap 822 should be affixed to each BET 90 after filling and before a filled medical syringe 810 is accessed from enclosing sub-kit bag 30, as seen in FIG. 39. Once capped, a medical syringe 810, being totally retained within inner bag 820, can be removed with assurance of safety both from contents of medical syringe 810 and maintenance of sterility of matter both inside and outside of medical syringe 810 as seen in FIG. 40. Such provides for use of medical syringe 810 by, using conventional technique, dropping medical syringe onto a sterile field 840, as seen in FIG. 41, with assurance of no degradation in sterility preparatory to use.

The invention claimed is:

1. Single use, completely enclosing convenience kits used for compounding medicine, selected from a group of convenience kits comprising sub-kits which sterilize medicine capable of being sterilized by filtration and sub-kits used for compounding raw medicine which should not be sterilized by filtration but which are compounded without degrading sterilization levels, such convenience kits being provided for compounding raw medicine provided in at least one pre-filled vial which is provided separately, each such kit, being pre-sterilized for use, providing safety via totally enclosed fluid communicating pathways for delivering and compounding medicine, each of said convenience kits comprising an exterior sub-kit for accessing, measuring and displacing fluids in a compounding process and an enclosing sub-kit for providing a closed, sterile housing for a vessel which is filled with a prescribed dose of compounded medicine, provided via a securely affixed, absolutely closed pathway from said exterior sub-kit for use in patient treatment.

2. Said exterior sub-kit according to claim 1 being a sub-kit which is used to displace all fluids disposed therein without communicating any of the fluids into the environment outside the exterior sub-kit, while performing as a fluid acquisition, displacement and measuring system for compounding a prescription which meets quantity and quality requirements of medicine prescribed, said exterior sub-kit comprising:
a manifold comprising adjustable control valves for variable access and fluid pathways for displacing medicine being compounded, said manifold further comprising a vial adapter for each vial to be accessed, each vial adapter comprising a vial spike for spiking a septum of a pre-filled vial, to thereby access the raw medicine contained therein and a vial adapter spike valve for maintaining closure of unused vial adapter spikes;
said manifold further comprising an additional control valve which provides a fluid control pathway interface with a first tether which comprises a length of flexible medical tubing which is affixed on a first end to a TMD syringe assembly comprising a TMD syringe disposed and fully contained within a plastic bag, said plastic bag being affixed via BET to said first tether outside said bag and to said TMD syringe inside said bag, and, on a second end, being securely affixed to said control valve disposed on the proximal end of said manifold;
said first tether comprising a length of flexible micro-tubing securely affixed on one end to said additional control valve and on the other end to said TMD syringe assembly, said length of flexible micro-tubing being sufficiently long to permit 180° rotation of said TMD syringe without displacing said manifold;
said manifold still further comprising a fluid pathway interface on an end of said manifold distal from said additional control valve which is closed by a second tether comprising a predetermined length of flexible medical tubing for communicating fluid from a TFP syringe assembly, an associated TFP syringe being releasably affixed to said manifold via a combination CLAVE/SPIROS component combination and said predetermined length being adequate for rotating said associated TFP syringe 180° without displacing said manifold assembly.

3. Said exterior sub-kit according to claim 2 wherein said exterior sub-kit further comprises a gas sterilizing assembly comprising a sterilizing filter and a one way valve whereby air can be drawn and sterilized into a TMD syringe for use in testing efficacy of a sterilizing filter.

4. Said enclosing sub-kit according to claim 1 being a sub-kit which is used to provide a totally enclosed housing for a vessel filling with medicine compounded via said exterior sub-kit for patient treatment, said enclosing sub-kit comprising a plastic bag providing a closed housing for apparatus residing therein in which all items are packed, sealed and pre-sterilized to provide a completed kit which has a predetermined SAL, said plastic bag having fluid access only from a group of bag entry technology assemblies comprising BET and BEST components securely affixed via closed pathways to an associated exterior sub-kit which assures maintenance of desired sterility for compounded medicine, received from said associated exterior sub-kit, which is displaced into patient treatment vessels selected from a group of vessels comprising elastomeric balls, syringes and IV bags.

5. Said enclosing sub-kit according to claim 4 further comprising flow pathways from said bag entry technologies through pathways comprising separable dripless connectors whereby said vessel can be detached from contacting communication with said bag entry technology components without fluid communication to the outside environment.

6. An interface according to claim 4 between said enclosing sub-kit and said exterior sub-kit according to claim 1 whereby fluid is dispensed from said exterior sub-kit into said enclosing sub-kit, without communicating any form of fluid into the surrounding environment, said interface comprising bag entry technology derived from a group of bag entry technologies comprising a single BEST assembly, a single BET assembly and a combination of BET and BEST technologies.

7. A convenience kit comprising an exterior sub-kit for displacing and communicating fully contained fluids from medicine containing source containers to an enclosing sub-kit housed in a closed plastic bag in which at least one pre-sterilized medicine container is disposed for being filled and capped before being accessed from said plastic bag to thereby provide finally compounded medicine for use, with resultant user safety and predetermined product SAL, said enclosed compounded medicine preparation process and product meeting regulatory requirements of USP 797 and USP 800 for compounding of such medical preparations.

* * * * *